US006451303B1

(12) United States Patent
Whitehouse et al.

(10) Patent No.: US 6,451,303 B1
(45) Date of Patent: Sep. 17, 2002

(54) METHOD OF TREATING CORONARY ARTERY DISEASE BY ADMINISTERING A RECOMBINANT FGF

(75) Inventors: Martha J. Whitehouse, San Francisco; W. Michael Kavanaugh, Marin, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/417,721

(22) Filed: Oct. 13, 1999

Related U.S. Application Data
(60) Provisional application No. 60/104,103, filed on Oct. 13, 1998.

(51) Int. Cl.$^7$ .................. A61K 31/00; A61K 38/00; A61K 38/16; A61K 45/00

(52) U.S. Cl. ............. 424/85.1; 424/184.1; 424/185.1; 424/198.1; 512/2; 512/12

(58) Field of Search .................. 514/2, 12; 530/300, 530/350, 351, 399; 424/184.1, 198.1, 185.1, 85.1

(56) References Cited

U.S. PATENT DOCUMENTS

| | | | |
|---|---|---|---|
| 4,296,100 A | 10/1981 | Franco | 424/108 |
| 4,378,347 A | 3/1983 | Franco | 424/108 |
| 4,956,455 A | 9/1990 | Esch et al. | 530/399 |
| 5,137,510 A | 8/1992 | VanDeripe | 604/28 |
| 5,137,734 A | 8/1992 | Spiegelman et al. | 424/574 |
| 5,155,214 A | 10/1992 | Baird et al. | 530/399 |
| 5,155,217 A | 10/1992 | Goldfarb et al. | 536/27 |
| 5,194,596 A * | 3/1993 | Tischer et al. | 530/399 |
| 5,213,570 A | 5/1993 | VanDeripe | 604/23 |
| 5,238,916 A | 8/1993 | Goldfarb et al. | 514/2 |
| 5,244,460 A | 9/1993 | Unger et al. | |
| 5,269,326 A | 12/1993 | Verrier | 128/642 |
| 5,286,252 A * | 2/1994 | Tuttle et al. | 604/20 |
| 5,302,702 A | 4/1994 | Seddon et al. | 530/399 |
| 5,310,883 A | 5/1994 | Seddon et al. | 530/399 |
| 5,314,872 A | 5/1994 | Kato et al. | 514/12 |
| 5,350,836 A * | 9/1994 | Kopchick et al. | 530/399 |
| 5,352,589 A | 10/1994 | Bergonzoni et al. | 435/69.4 |
| 5,371,206 A | 12/1994 | Seddon et al. | 536/23.5 |
| 5,387,673 A | 2/1995 | Seddon et al. | 530/399 |
| 5,439,818 A | 8/1995 | Fiddes et al. | 435/240.2 |
| 5,464,774 A | 11/1995 | Baird et al. | 536/23.51 |
| 5,491,220 A | 2/1996 | Seddon et al. | 530/399 |
| 5,514,566 A | 5/1996 | Fiddes et al. | 435/69.1 |
| 5,604,293 A | 2/1997 | Fiddes et al. | 530/399 |
| 5,750,659 A | 5/1998 | Basiclico et al. | 530/399 |
| 5,792,453 A | 8/1998 | Hammond et al. | |

FOREIGN PATENT DOCUMENTS

| | | |
|---|---|---|
| EP | 0 228 449 B1 | 12/1986 |
| WO | WO 89/04832 | 6/1989 |

OTHER PUBLICATIONS

Vukicevic et al. Induction of nephrogenic mesenchyme by osteogenic protein 1 (bone morphogenetic protein 7). Proc Natl Acad Sci USA 93: 9021–9026, 1996.*
Massague et al. The TFG–beta family of growth and differentiation factors. Cell 49: 437–438, 1987.*
Pilbeam et al. Comparison of the effects of various lengths of synthetic human parathyroid hormone–related peptide (hPTHrP) of malignancy on resorption and formation in organ culture. Bone 14: 717–720, 1993.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Benjamin et al. A plasticity window for blood vessel remodelling is defined by pericyte coverage of the preformed endothelial network and is regulated by PDGF–B and VEGF. Development 125: 1591–1598, 1998.*

(List continued on next page.)

Primary Examiner—Elizabeth Kemmerer
Assistant Examiner—Bridget E. Bunner
(74) Attorney, Agent, or Firm—Leslie T. Henry; Lisa E. Alexander; Robert P. Blackburn

(57) ABSTRACT

The present invention has multiple aspects. In particular, in one aspect, the present invention is directed to a unit dose comprising 0.2 μg/kg to 36 μg/kg of a recombinant FGF or an angiogenically active fragment or mutein thereof. In another aspect, the present invention is directed to a pharmaceutical composition comprising an angiogenically effective dose of an FGF or an angiogenically active fragment or mutein thereof, and a pharmaceutically acceptable carrier. Typically, the angiogenically effective dose comprises 0.2 μg/kg to 36 μg/kg of an FGF of any one of SEQ ID NOS: 1–3, 5, 8–10 or 12–14 or an angiogenically active fragment or mutein thereof. In yet another aspect, the present invention is directed to a method for treating a human patient for coronary artery disease, comprising administering into at least one coronary vessel of a human patient in need of treatment for coronary artery disease a safe and angiogenically effective dose of a recombinant FGF of any one of SEQ ID NOS: 1–3, 5, 8–10 or 12–14, or an angiogenically active fragment or mutein thereof.

7 Claims, 2 Drawing Sheets

OTHER PUBLICATIONS

Galzie et al. Fibroblast growth factors and their receptors. Biochem Cell Biol 75: 669–685, 1997.*

Seno et al. Carboxyl–terminal structure of basic fibroblast growth factor significantly contributes to its affinity for heparin. Eur. J. Biochem. 188: 239–245, 1990.*

Fox et al. Production, biological activity, and structure of recombinant basic fibroblast growth factor and an analog with cysteine replaced by serine. J. Biol. Chem. 263: 18452–18458, 1988.*

Bikfalvi et al. (1997), "Biological Roles of Fibroblast Growth Factor–2," Endocrine Reviews 18: 26–45.

Nabel et al. (1993), "Recombinant Fibroblast Growth Factor–1 Promotes Intimal Hyperplasia and Angiogenesis in Arteries In Vivo," Nature 362: 844–846.

Folkman, Angiogenic Therapy of the Human Heart, Circulation, 97:628–629 (1998).

Kirschner, et al., Basic fibroblast growth factor protects agains ecitotoxicity and chemical hypoxia in both neonatal and adult rats. Journal of Cerebral Blood Flow and Metabolish, 15(4):619–623 (1995).

Sellke et al., Angiogenesis induced by acidic fibroblast growth factor as an alternative method of reva scularization for chronic myocardial ischemia, Surgery 120(2):82–188 (1996).

Laham, et al., Intrapericardial Delivery of Fibroblast Growth Factor–2 Induces Neovascularization in a Procine Model of Chronic Myocardial Ischemia, The Journal of Pharmacology and Experimental Therapeutics, 292(2):795–802 (Oct. 21, 1999).

Abraham, et al., Human basic fibroblast growth factor: nucleotide sequence and genomic organization, The EMBO Journal, 5(10):2523–2528 (1986).

Anderson, Gene Therapy for Genetic Diseases, Human Gene Therapy 5:281–282 (1994).

Banai, et al., Angiogenic–Induced Enhancement of Collateral Blood Flow to Ischemic Myocardium by Vascular Endothelial Growth Factor in Dogs, Circulation, 89(5):2183–2189 (May, 1994).

Barinaga, Step Taken Toward Improved Vectors for Gene Transfer, Science 266:1326 (Nov. 25, 1994).

Barr, et al., Efficient catheter–mediated gene transfer into the heart using replication–defective adenovirus, Gene Therapy 1:51–58 (1994).

Battler, et al., Intracoronary Injection of Basic Fibroblast Growth Factor Enhances Angiogenesis in Infarcted Swine Myocardium, JACC, 22(7):2001–2006 (Dec., 1993).

Brown, Gene Therapy 'Oversold' by Researchers, Journalists, The Washington Post, A1 & A22 (Dec. 8, 1995).

Burgess, et al., The Heparin–Binding (Fibroblast) Growth Factor Family of Proteins, Annu. Rev.Biochem, 58:575–606 (1989).

Challita, et al., Lack of expression from a retroviral vector after transduction of murine hematopoietic stem cells is associated with methylation in vivo, Proc. Natl. Acad. Sci. USA 91:2567–2571 (Mar., 1994).

Clements, et al., Activation of fibroblast growth factor(FGF) receptors by recombinant human FGF–5, Oncogene, 8:1311–1316 (1993).

Coghlan, Gene dream fades away, New Scientist 148(2005):14–15 (Nov. 25, 1995).

Corallini, et al., Promotion of tumour metastases and induction of angiogenesis by native HIV–1 Tat protein from BK virus/tat transgenic mice, AIDS 10(7):701–710 (1996).

Coulier, et al., Putative structure of the FGF6 gene product and role of the signal peptide, Oncogene, 6:1437–1444 (1991).

Fisher, et al., Recombinant adeno–associated virus for muscle directed gene therapy, Nature Medicine 3(3):306–312 (Mar., 1997).

Giordano, et al., Reduced Myocardial Ischemia After Recombinant Adenovirus Mediated in–Vivo Fibroblast Growth Factor–5 Gene Transfer, J. Invest. Med. 3:278A (1995).

Giordano, et al., Intracoronary gene transfer of fibroblast growth factor–5 increases blood flow and contractile function in an ischemic region of the heart, Nature Medicine 2(5):534–539 (May, 1996).

Guzman, et al., Efficient Gene Transfer Into Myocardium by Direct Injection of Adenovirus Vectors, Circulation Research 73(6):1202–1207 (Dec., 1993).

Harada, et al., Basic Fibroblast Growth Factor Improves Myocardial Function in Chronically Ischemic Porcine Hearts, J. Clin. Invest. 94:623–630 (Aug., 1994).

Jaroff, Keys to the Kingdom, Time 148(14):24–29 (1996).

Kass–Eisler, et al. Quantitative determination of adenovirus–mediated gene delivery to rat cardiac myocytes in vitro and in vivo, Proc. Natl. Acad. Sci. USA 90:11498–11502 (Dec., 1993).

Klagsbrun, Angiogenic Factors: Regulators of Blood Supply–Side Biology, The New Biologist, 3(8):745–749 (Aug., 1991).

Landau, et al., Intrapericardial basic fibroblast growth factor induces myocardial angiogenesis in a rabbit model of chronic ischemia, American Heart Journal, 129(5):924–931 (May, 1995).

Lazarous, et al., Comparative Effects of Basic Fibroblast Growth Factor and Vascular Endothelial Growth Factor on Coronary Collateral Development and the Arterial Response to Injury, Circulation, 94(5):1075–1082 (Sep. 1, 1996).

Lazarous, et al., Effects of Chronic Systemic Administration of Basic Fibroblast Growth Factor on Collateral Development in the Canine Heart, Circulation 91(1):145–153 (Jan. 1, 1995).

Lipton, et al., Acidic fibroblast growth factor enhances regeneration of processes by postnatal mammalian retinal ganglion cells in culture, Proc. Natl. Acad. Sci., USA 85:2388–2392 (Apr., 1988).

Magovern, et al., Direct in vivo Gene Transfer to Canine Myocardium Using a Replication–Deficient Adenovirus Vector, Ann. Thorac. Surg. 62:425–34 (1996).

Marshall, Gene Therapy's Growing Pains, Science, 269:1050–1055 (Aug. 25, 1995).

Nahreinei, et al., Versatile adeno–associated virus 2–based vectors for construction recombinant virions, Gene 124:257–262 (1993).

Ohno, et al., Gene Therapy for Vascular Smooth Muscle Cell Proliferation After Arterial Injury, Science 265:781–784 (Aug. 5, 1994).

Orkin, et al., Report and Recommendations of the Panel to Assess the NIH Investment in Research on Gene Therapy, (Dec. 7, 1995) 41 pages.

Rakusan, K., Coronary Angiogenesis, Annals New York Academy of Sciences, 752:257–265 (1995).

Rubin, et al., Purification and characterization of a newly identified growth factor specific for epithelial cells, Proc. Natl. Acad. Sci. USA, 86:802–806 (Feb., 1989).

Schubert, et al., Multiple Influences of a Heparin–binding Growth Factor on Neuronal Development, The Journal of Cell Biology, 104:635–643 (1987).

Shou, et al., Effect of Basic Fibroblast Growth Factor on Myocardial Angiogenesis in Dogs With Mature Collateral Vessels, JACC, 29(5):1102–1106 (Apr., 1997).

Slavin, Fibroblast Growth Factors: At the Heart of Angiogenesis, Cell Biology International, 19(5):431–444 (1995).

Unger, et al., Basic fibroblast growth factor enhances myocardial collateral flow in a canine model, Am J. Physiol 266 (Heart Circ. Physiol 35):H1588–H1595, (1994).

Valles, et al., Acidic fibroblast growth factor is a modulator of epithelial plasticity in a rat bladder carcinoma cell line, Proc. Natl. Acad. Sci. USA, 87:1124–1128 (Feb., 1990).

Xiao, et al., Efficient Long–Term Gene Transfer into Muscle Tissue of Immunocompetent Mice by Adeno–Associated Virus Vector, Journal of Virology, 70:8098–8108 (Nov., 1996).

Yanagisawa–Miwa, et al., Salvage of Infarcted Myocardium by Angiogenic Action of Basic Fibroblast Growth Factor, Science 257:1401–1403 (Sep. 4, 1992).

Yayon, et al., Autocrine Regulation of cell growth and transformation by basic fibroblast growth factor, Cancer and Metastasis Reviews 9:191–202 (1990).

Laham, et al., Local Perivascular Basic Fibroblast Growth Factor (bFGF) Treatment in Patients With Ischemic Heart Disease, J. Am. Coll. Cardiol., 31:394A.

Lopez, et al., Local Perivascular Administration of Basic Fibroblast Growth Factor: Drug Delivery and Toxicological Evaluation, Drug and Metabolism and Disposition, 24(8):922–924 (1996).

Mathieu, et al., Receptor Binding and Mitogenic Properties of Mouse Fibroblast Growth Factor 3, The Journal of Biological Chemistry, 270(41):24197–24203 (1995).

Miyamoto, et al., Molecular Cloning of a Novel Cytokine cDNA Encoding the Ninth Member of the Fibroblast Growth Factor Family, Which has a Unique Secretion Property, Molecular and Cellular Biology, 13(7):4251–4259 (Jul., 1993).

Miyataka, et al., Basic Fibroblast Growth Factor Increased Regional Myocardial Blood Flow and Limited Infarct Size of Acutely Infarcted Myocardium in Dogs, Angiology, 49(5):381–390 (May, 1998).

Ornitz, et al., Receptor Specificity of the Fibroblast Growth Factor Family, The Journal of Biological Chemistry, 271(25):15292015297 (Jun. 21, 1996).

Schumacher, et al., Induction of Neoangiogenesis in Ischemic Myocardium by Human Growth Factors, Circulation, 97:645–650 (1997).

Sellke, et al., Basic FGF enhances endothelium–dependent relaxation of the collateral–perfused coronary microcirculation, The Amerian Physiological Society, 267:H1303–H1311 (1994).

Sellke, et al., Enhanced microvascular relaxations to VEGF and bFGF in chronically ischemic porcine myocardium, Am. J. Physiol., 271:H713–H720 (1996).

Sellke, et al., Therapeutic Angiogenesis With Basic Fibroblast Growth Factor: Technique and Early Results, The Society of Thoracic Surgeons, 65:1540–1544 (1998).

Uchida, et al., Angiogenic therapy of acute myocardial infarction by intrapericardial injection of basic fibroblast growth factor and heparin sulfate: An experimental study, American Heart Journal, 130(6):1182–1188 (Dec., 1995).

Watanabe, et al., Effect of basic fibroblast growth factor on angiogenesis in the infarcted porcine heart, Basic Res Cardiol., 93:30–37 (1998).

* cited by examiner

SEQUENCE LISTING

```
<160> NUMBER OF SEQ ID NOS: 15

<210> SEQ ID NO 1
<211> LENGTH: 140
<212> TYPE: PRT
<213> ORGANISM: Human FGF-1

<400> SEQUENCE: 1

Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Tyr Asp
            20                  25                  30

Gly Thr Arg Asp Arg Ser Asp Gln His Ile Gln Leu Gln Leu Ser Ala
        35                  40                  45

Glu Ser Tyr Gly Glu Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Tyr Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Tyr Ser Ser Asp
    130                 135                 140

<210> SEQ ID NO 2
<211> LENGTH: 140
<212> TYPE: PRT
<213> ORGANISM: bovine FGF-1

<400> SEQUENCE: 2

Phe Asn Leu Pro Leu Gly Asn Tyr Lys Lys Pro Lys Leu Leu Tyr Cys
 1               5                  10                  15

Ser Asn Gly Gly Tyr Phe Leu Arg Ile Leu Pro Asp Gly Thr Val Asp
            20                  25                  30

Gly Thr Lys Asp Arg Ser Asp Gly His Ile Gln Leu Phe Leu Cys Ala
        35                  40                  45

Glu Ser Ile Gly Glu Val Tyr Ile Lys Ser Thr Glu Thr Gly Gln Phe
    50                  55                  60

Leu Ala Met Asp Thr Asp Gly Leu Leu Tyr Gly Ser Gln Thr Pro Asp
65                  70                  75                  80
```

```
Glu Glu Cys Leu Phe Leu Glu Arg Leu Glu Glu Asn His Tyr Asn Thr
             85                  90                  95

Tyr Ile Ser Lys Lys His Ala Glu Lys His Trp Phe Val Gly Leu Lys
            100                 105                 110

Lys Asn Gly Arg Ser Lys Leu Glu Pro Arg Thr His Phe Gly Gln Lys
            115                 120                 125

Ala Ile Leu Phe Leu Pro Leu Pro Val Ser Ser Asp
            130                 135                 140

<210> SEQ ID NO 3
<211> LENGTH: 146
<212> TYPE: PRT
<213> ORGANISM: Human FGF-2

<400> SEQUENCE: 3

Pro Ala Leu Pro Glu Asp Gly Gly Ser Gly Ala Phe Pro Pro Gly His
  1               5                  10                  15

Phe Lys Asp Pro Lys Arg Leu Tyr Cys Lys Asn Gly Gly Phe Phe Leu
             20                  25                  30

Arg Ile His Pro Asp Gly Arg Val Asp Gly Val Arg Glu Lys Ser Asp
         35                  40                  45

Pro His Ile Lys Leu Gln Leu Gln Ala Glu Glu Arg Gly Val Val Ser
     50                  55                  60

Ile Lys Gly Val Cys Ala Asn Arg Tyr Leu Ala Met Lys Glu Asp Gly
 65                  70                  75                  80

Arg Leu Leu Ala Ser Lys Cys Val Thr Asp Glu Cys Phe Phe Phe Glu
             85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
            130                 135                 140

Lys Ser
145

<210> SEQ ID NO 4
<211> LENGTH: 442
<212> TYPE: DNA
<213> ORGANISM: bovine FGF-2
<220> FEATURE:
<221> NAME/KEY: CDS
<222> LOCATION: (1)..(438)

<400> SEQUENCE: 4 cca gcc cta cca gaa gat ggg ggg tcc ggg gcc ttc cca cca ggg cac      48
Pro Ala Leu Pro Glu Asp Gly Gly Ser Gly Ala Phe Pro Pro Gly His
  1               5                  10                  15 ttc aaa gat cca aaa cga cta tat tgt aaa aac ggg ggg ttc ttc cta      96
Phe Lys Asp Pro Lys Arg Leu Tyr Cys Lys Asn Gly Gly Phe Phe Leu
             20                  25                  30 cga atc cac cca gat ggg cga gta gat ggg gta cga gaa aaa tcc gat     144
Arg Ile His Pro Asp Gly Arg Val Asp Gly Val Arg Glu Lys Ser Asp
         35                  40                  45 cca cac atc aaa cta caa cta caa gcc gaa gaa cga ggg gta gta tcc     192
Pro His Ile Lys Leu Gln Leu Gln Ala Glu Glu Arg Gly Val Val Ser
     50                  55                  60 atc aaa ggg gta tgt gcc aac cga tat cta gcc atg aaa gaa gat ggg     240
Ile Lys Gly Val Cys Ala Asn Arg Tyr Leu Ala Met Lys Glu Asp Gly
```

```
                65                  70                  75                  80
cga cta cta gcc tcc aaa tgt gta acc gat gaa tgt ttc ttc ttc gaa        288
Arg Leu Leu Ala Ser Lys Cys Val Thr Asp Glu Cys Phe Phe Phe Glu
                    85                  90                  95 cga cta gaa tcc aac aac tat aac acc tat cga tcc cga aaa tat tcc        336
Arg Leu Glu Ser Asn Asn Tyr Asn Thr Tyr Arg Ser Arg Lys Tyr Ser
                100                 105                 110 tcc tgg tat gta gcc cta aaa cga acc ggg caa tat aaa cta ggg cca        384
Ser Trp Tyr Val Ala Leu Lys Arg Thr Gly Gln Tyr Lys Leu Gly Pro
            115                 120                 125 aaa acc ggg cca ggg caa aaa gcc atc cta ttc cta cca atg tcc gcc        432
Lys Thr Gly Pro Gly Gln Lys Ala Ile Leu Phe Leu Pro Met Ser Ala
        130                 135                 140 aaa tcc taag                                                           442
Lys Ser
145
```

<210> SEQ ID NO 5
<211> LENGTH: 146
<212> TYPE: PRT
<213> ORGANISM: bovine FGF-2

<400> SEQUENCE: 5

```
Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe Leu
                20                  25                  30

Arg Ile His Pro Asp Gly Arg Val Asp Gly Val Arg Glu Lys Ser Asp
            35                  40                  45

Pro His Ile Lys Leu Gln Leu Gln Ala Glu Glu Arg Gly Val Val Ser
        50                  55                  60

Ile Lys Gly Val Cys Ala Asn Arg Tyr Leu Ala Met Lys Glu Asp Gly
 65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Gly Pro Gly Gln Lys Ala Ile Leu Phe Leu Pro Met Ser Ala
    130                 135                 140

Lys Ser
145
```

<210> SEQ ID NO 6
<211> LENGTH: 9
<212> TYPE: PRT
<213> ORGANISM: Bovis bovinus

<400> SEQUENCE: 6

```
Met Ala Ala Gly Ser Ile Thr Thr Leu
 1               5
```

<210> SEQ ID NO 7
<211> LENGTH: 240
<212> TYPE: PRT
<213> ORGANISM: Murine FGF-3

<400> SEQUENCE: 7

-continued

Met Gly Leu Ile Trp Leu Leu Leu Ser Leu Leu Glu Pro Ser Trp
1               5                   10                  15

Pro Thr Thr Gly Pro Gly Thr Arg Leu Arg Arg Asp Ala Gly Gly Arg
            20                  25                  30

Gly Gly Val Tyr Glu His Leu Gly Ala Pro Arg Arg Lys Leu
        35                  40                  45

Tyr Cys Ala Thr Lys Tyr His Leu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Val Val Ala Ile Lys Gly Leu Phe Ser Gly Arg Tyr
                85                  90                  95

Leu Ala Met Asn Lys Arg Gly Arg Leu Tyr Ala Ser Asp His Tyr Asn
            100                 105                 110

Ala Glu Cys Glu Phe Val Glu Arg Ile His Glu Leu Gly Tyr Asn Thr
        115                 120                 125

Tyr Ala Ser Arg Leu Tyr Arg Thr Gly Ser Ser Gly Pro Gly Ala Gln
    130                 135                 140

Arg Gln Pro Gly Ala Gln Arg Pro Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Gly His Lys Asp His Glu Met Val Arg
            180                 185                 190

Leu Leu Gln Ser Ser Gln Pro Arg Ala Pro Gly Glu Gly Ser Gln Pro
        195                 200                 205

Arg Gln Arg Arg Gln Lys Lys Gln Ser Pro Gly Asp His Gly Lys Met
    210                 215                 220

Glu Thr Leu Ser Thr Arg Ala Thr Pro Ser Thr Gln Leu His Thr Gly
225                 230                 235                 240

<210> SEQ ID NO 8
<211> LENGTH: 205
<212> TYPE: PRT
<213> ORGANISM: Human FGF-4

<400> SEQUENCE: 8

Ser Gly Pro Gly Thr Ala Ala Val Ala Leu Leu Pro Ala Val Leu Leu
1               5                   10                  15

Ala Leu Leu Ala Pro Trp Ala Gly Arg Gly Gly Ala Ala Ala Pro Thr
            20                  25                  30

Ala Pro Asn Gly Thr Leu Glu Ala Glu Leu Glu Arg Arg Trp Glu Ser
        35                  40                  45

Leu Val Ala Leu Ser Leu Ala Arg Leu Pro Val Ala Ala Gln Pro Lys
    50                  55                  60

Glu Ala Ala Val Gln Ser Gly Ala Gly Asp Tyr Leu Leu Gly Ile Lys
65                  70                  75                  80

Arg Leu Arg Arg Leu Tyr Cys Asn Val Gly Ile Gly Phe His Leu Gln
                85                  90                  95

Ala Leu Pro Asp Gly Arg Ile Gly Gly Ala His Ala Asp Thr Arg Asp
            100                 105                 110

Ser Leu Leu Glu Leu Ser Pro Val Glu Arg Gly Val Val Ser Ile Phe
        115                 120                 125

Gly Val Ala Ser Arg Phe Phe Val Ala Met Ser Ser Lys Gly Lys Leu
    130                 135                 140

-continued

Tyr Gly Ser Pro Phe Phe Thr Asp Glu Cys Thr Phe Lys Glu Ile Leu
145                 150                 155                 160

Leu Pro Asn Asn Tyr Asn Ala Tyr Glu Ser Tyr Lys Tyr Pro Gly Met
            165                 170                 175

Phe Ile Ala Leu Ser Lys Asn Gly Lys Thr Lys Gly Asn Arg Val
        180                 185                 190

Ser Pro Thr Met Lys Val Thr His Phe Leu Pro Arg Leu
        195                 200                 205

<210> SEQ ID NO 9
<211> LENGTH: 266
<212> TYPE: PRT
<213> ORGANISM: Human FGF-5

<400> SEQUENCE: 9

Ser Leu Ser Phe Leu Leu Leu Phe Phe Ser His Leu Ile Leu Ser
1               5                   10                  15

Ala Trp Ala His Gly Glu Lys Arg Leu Ala Pro Lys Gly Gln Pro Gly
            20                  25                  30

Pro Ala Ala Thr Asp Arg Asn Pro Arg Gly Ser Ser Ser Arg Gln Ser
        35                  40                  45

Ser Ser Ser Ala Met Ser Ser Ser Ala Ser Ser Pro Ala Ala
    50                  55                  60

Ser Leu Gly Ser Gln Gly Ser Gly Leu Glu Gln Ser Ser Phe Gln Trp
65                  70                  75                  80

Ser Leu Gly Ala Arg Thr Gly Ser Leu Tyr Cys Arg Val Gly Ile Gly
                85                  90                  95

Phe His Leu Gln Ile Tyr Pro Asp Gly Lys Val Asn Gly Ser His Glu
            100                 105                 110

Ala Asn Met Leu Ser Val Leu Glu Ile Phe Ala Val Ser Gln Gly Ile
        115                 120                 125

Val Gly Ile Arg Gly Val Phe Ser Asn Lys Phe Leu Ala Met Ser Lys
    130                 135                 140

Lys Gly Lys Leu His Ala Ser Ala Lys Phe Thr Asp Asp Cys Lys Phe
145                 150                 155                 160

Arg Glu Arg Phe Gln Glu Asn Ser Tyr Asn Thr Tyr Ala Ser Ala Ile
                165                 170                 175

His Arg Thr Glu Lys Thr Gly Arg Glu Trp Tyr Val Ala Leu Asn Lys
            180                 185                 190

Arg Gly Lys Ala Lys Arg Gly Cys Ser Pro Arg Val Lys Pro Gln His
        195                 200                 205

Ile Ser Thr His Phe Leu Pro Arg Phe Lys Gln Ser Glu Gln Pro Glu
    210                 215                 220

Leu Ser Phe Thr Val Thr Val Pro Glu Lys Lys Lys Pro Pro Ser Pro
225                 230                 235                 240

Ile Lys Pro Lys Ile Pro Leu Ser Ala Pro Arg Lys Asn Thr Asn Ser
                245                 250                 255

Val Lys Tyr Arg Leu Lys Phe Arg Phe Gly
            260                 265

<210> SEQ ID NO 10
<211> LENGTH: 207
<212> TYPE: PRT
<213> ORGANISM: Human FGF-6

<400> SEQUENCE: 10

```
Ala Leu Gly Gln Lys Leu Phe Ile Thr Met Ser Arg Gly Ala Gly Arg
 1               5                  10                  15

Leu Gln Gly Thr Leu Trp Ala Leu Val Phe Leu Gly Ile Leu Val Gly
            20                  25                  30

Met Val Val Pro Ser Pro Ala Gly Thr Arg Ala Asn Asn Thr Leu Leu
        35                  40                  45

Asp Ser Arg Gly Trp Gly Thr Leu Leu Ser Arg Ser Arg Ala Gly Leu
    50                  55                  60

Ala Gly Glu Ile Ala Gly Val Asn Trp Glu Ser Gly Tyr Leu Val Gly
65                  70                  75                  80

Ile Lys Arg Gln Arg Arg Leu Tyr Cys Asn Val Gly Ile Gly Phe His
                85                  90                  95

Leu Gln Val Leu Pro Asp Gly Arg Ile Ser Gly Thr His Glu Glu Asn
                100                 105                 110

Pro Tyr Ser Leu Leu Glu Ile Ser Thr Val Glu Arg Gly Val Val Ser
            115                 120                 125

Leu Phe Gly Val Arg Ser Ala Leu Phe Val Ala Met Asn Ser Lys Gly
130                 135                 140

Arg Leu Tyr Ala Thr Pro Ser Phe Gln Glu Glu Cys Lys Phe Arg Glu
145                 150                 155                 160

Thr Leu Leu Pro Asn Asn Tyr Asn Ala Tyr Glu Ser Asp Leu Tyr Gln
                165                 170                 175

Gly Thr Tyr Ile Ala Leu Ser Lys Tyr Gly Arg Val Lys Arg Gly Ser
            180                 185                 190

Lys Val Ser Pro Ile Met Thr Val Thr His Phe Leu Pro Arg Ile
            195                 200                 205

<210> SEQ ID NO 11
<211> LENGTH: 193
<212> TYPE: PRT
<213> ORGANISM: Human FGF-7

<400> SEQUENCE: 11

Met His Lys Trp Ile Leu Thr Trp Ile Leu Pro Thr Leu Leu Tyr Arg
 1               5                  10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
```

```
                    165                 170                 175
Lys Lys Thr Lys Lys Gln Lys Thr Ala His Phe Leu Pro Met Ala Ile
                180                 185                 190
Thr
```

<210> SEQ ID NO 12
<211> LENGTH: 215
<212> TYPE: PRT
<213> ORGANISM: Murine FGF-8

<400> SEQUENCE: 12

```
Met Gln Ser Pro Arg Ser Ala Leu Ser Cys Leu Leu Leu His Leu Leu
  1               5                  10                  15
Val Leu Cys Leu Gln Ala Gln Val Thr Val Gln Ser Ser Pro Asn Phe
                 20                  25                  30
Thr Gln His Val Arg Glu Gln Ser Leu Val Thr Asp Gln Leu Ser Arg
             35                  40                  45
Arg Leu Ile Arg Thr Tyr Gln Leu Tyr Ser Arg Thr Ser Gly Lys His
         50                  55                  60
Val Gln Val Leu Ala Asn Lys Arg Ile Asn Ala Met Ala Phe Asp Gln
 65                  70                  75                  80
Asp Pro Phe Ala Lys Leu Ile Val Glu Tyr Asp Thr Phe Gly Ser Arg
                 85                  90                  95
Val Arg Val Arg Gly Ala Glu Thr Gly Leu Tyr Ile Cys Met Asn Lys
                100                 105                 110
Lys Gly Lys Leu Ile Ala Lys Ser Asn Gly Lys Gly Lys Asp Cys Val
            115                 120                 125
Phe Thr Phe Ile Val Ile Glu Asn Asn Tyr Thr Ala Leu Gln Asn Ala
130                 135                 140
Lys Tyr Glu Gly Trp Tyr Met Ala Phe Thr Ala Lys Gly Arg Pro Arg
145                 150                 155                 160
Lys Gly Ser Lys Thr Arg Gln His Gln Arg Glu Val His Phe Met Lys
                165                 170                 175
Arg Leu Pro Arg Gly His His Thr Thr Glu Gln Ser Leu Arg Phe Glu
                180                 185                 190
Phe Leu Asn Tyr Pro Pro Phe Thr Arg Ser Leu Arg Gly Ser Gln Arg
            195                 200                 205
Thr Trp Ala Pro Glu Pro Arg
        210                 215
```

<210> SEQ ID NO 13
<211> LENGTH: 208
<212> TYPE: PRT
<213> ORGANISM: Human FGF-9

<400> SEQUENCE: 13

```
Met Ala Pro Leu Gly Glu Val Gly Asn Tyr Phe Gly Val Gln Asp Ala
  1               5                  10                  15
Val Pro Phe Gly Asn Val Pro Val Leu Pro Val Asp Ser Pro Val Leu
                 20                  25                  30
Leu Ser Asp His Leu Gly Gln Ser Glu Ala Gly Gly Leu Pro Arg Gly
             35                  40                  45
Pro Ala Val Thr Asp Leu Asp His Leu Lys Gly Ile Leu Arg Arg Arg
         50                  55                  60
Gln Leu Tyr Cys Arg Thr Gly Phe His Leu Glu Ile Phe Pro Asn Gly
 65                  70                  75                  80
```

```
Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
        130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 14
<211> LENGTH: 207
<212> TYPE: PRT
<213> ORGANISM: Human FGF-98

<400> SEQUENCE: 14

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205
```

<210> SEQ ID NO 15
<211> LENGTH: 266
<212> TYPE: PRT
<213> ORGANISM: Human FGF-5

<400> SEQUENCE: 15

-continued

```
Ser Leu Ser Phe Leu Leu Leu Leu Phe Phe Ser His Leu Ile Leu Ser
 1               5                   10                  15

Ala Trp Ala His Gly Glu Lys Arg Leu Ala Pro Lys Gly Gln Pro Gly
            20                  25                  30

Pro Ala Ala Thr Asp Arg Asn Pro Arg Gly Ser Ser Ser Arg Gln Ser
            35                  40                  45

Ser Ser Ser Ala Met Ser Ser Ser Ala Ser Ser Ser Pro Ala Ala
        50              55              60

Ser Leu Gly Ser Gln Gly Ser Gly Leu Glu Gln Ser Ser Phe Gln Trp
 65              70                  75                      80

Ser Leu Gly Ala Arg Thr Gly Ser Leu Tyr Cys Arg Val Gly Ile Gly
            85                  90                  95

Phe His Leu Gln Ile Tyr Pro Asp Gly Lys Val Asn Gly Ser His Glu
            100                 105                 110

Ala Asn Met Leu Ser Val Leu Glu Ile Phe Ala Val Ser Gln Gly Ile
            115                 120                 125

Val Gly Ile Arg Gly Val Phe Ser Asn Lys Phe Leu Ala Met Ser Lys
        130             135                 140

Lys Gly Lys Leu His Ala Ser Ala Lys Phe Thr Asp Asp Cys Lys Phe
145                 150                 155                 160

Arg Glu Arg Phe Gln Glu Asn Ser Tyr Asn Thr Tyr Ala Ser Ala Ile
                165                 170                 175

His Arg Thr Glu Lys Thr Gly Arg Glu Trp Tyr Val Ala Leu Asn Lys
            180                 185                 190

Arg Gly Lys Ala Lys Arg Gly Cys Ser Pro Arg Val Lys Pro Gln His
        195                 200                 205

Ile Ser Thr His Phe Leu Pro Arg Phe Lys Gln Ser Glu Gln Pro Glu
    210                 215                 220

Leu Ser Phe Thr Val Thr Val Pro Glu Lys Lys Asn Pro Pro Ser Pro
225                 230                 235                 240

Ile Lys Ser Lys Ile Pro Leu Ser Ala Pro Arg Lys Asn Thr Asn Ser
                245                 250                 255

Val Lys Tyr Arg Leu Lys Phe Arg Phe Gly
            260                 265
```

METHOD OF TREATING CORONARY ARTERY DISEASE BY ADMINISTERING A RECOMBINANT FGF

This application claims priority to U.S. provisional Application No. 60/104,103, filed Oct. 13, 1998.

BACKGROUND OF THE INVENTION

A. Field of the Invention

The present invention is directed to a unit dose comprising an FGF or an angiogenically active fragment or mutein thereof for inducing cardiac angiogenesis in a human. The present invention is also directed to a pharmaceutical composition comprising the unit dose of the FGF and to a method for administering this pharmaceutical composition to a human to induce cardiac angiogenesis while minimizing systemic risk to the patient. The present invention is useful because the unit dose, pharmaceutical composition and the method for its administration provide an alternative to surgical intervention for the treatment of coronary artery disease (CAD) and may further provide an adjunct for reducing post myocardial infarct (MI) injury in humans.

B. Background of the Invention

The fibroblast growth factors (FGF) are a family of at least eighteen structurally related polypeptides (named FGF-1 to FGF-18) that are characterized by a high degree of affinity for proteoglycans, such as heparin. The various FGF molecules range in size from 15–23 kD, and exhibit a broad range of biological activities in normal and malignant conditions including nerve cell adhesion and differentiation [Schubert et al., *J. Cell Biol.* 104:635–643 (1987)]; wound healing [U.S. Pat. No. 5,439,818 (Fiddes)]; as mitogens toward many mesodermal and ectodermal cell types, as trophic factors, as differentiation inducing or inhibiting factors [Clements, et al., *Oncogene* 8:1311–1316 (1993)]; and as an angiogenic factor [Harada, *J. Clin. Invest.*, 94:623–630 (1994)]. Thus, the FGF family is a family of pluripotent growth factors that stimulate to varying extents fibroblasts, smooth muscle cells, epithelial cells and neuronal cells.

When FGF is released by normal tissues, such as in fetal development or wound healing, it is subject to temporal and spatial controls. However, many of the members of the FGF family are also oncogenes. Thus, in the absence of temporal and spatial controls, they have the potential to stimulate tumor growth by providing angiogenesis.

Coronary artery disease (atherosclerosis) is a progressive disease in humans wherein one or more coronary arteries gradually become occluded through the buildup of plaque. The coronary arteries of patients having this disease are often treated by balloon angioplasty or the insertion of stents to prop open the partially occluded arteries. Ultimately, these patients are required to undergo coronary artery bypass surgery at great expense and risk. It would be desirable to provide such patients with a medicament that would enhance coronary blood flow so as to preclude the need to undergo bypass surgery.

An even more critical situation arises in humans when a patient suffers a myocardial infarction, wherein one or more coronary arteries or arterioles becomes completely occluded, such as by a clot. There is an immediate need to regain circulation to the portion of the myocardium served by the occluded artery or arteriole. If the lost coronary circulation is restored within hours of the onset of the infarction, much of the damage to the myocardium that is downstream from the occlusion can be prevented. The clot-dissolving drugs, such as tissue plasminogen activator (tPA), streptokinase, and urokinase, have been proven to be useful in this instance. However, as an adjunct to the clot dissolving drugs, it would also be desirable to also obtain collateral circulation to the damaged or occluded myocardium by angiogenesis.

Accordingly, it is an object of the present invention to provide a medicament and a mode of administration that provides human patients with cardiac angiogenesis during coronary artery disease and/or post acute myocardial infarction. More particularly, it is a further object of the present invention to provide a therapeutic dose of a mammalian FGF and a mode of administration to humans that provide the desired property of cardiac angiogenesis, while minimizing adverse effects.

Many of the various FGF molecules have been isolated and administered to various animal models of myocardial ischemia with varying and often times opposite results. According to Battler et al., "the canine model of myocardial ischemia has been criticized because of the abundance of naturally occurring collateral circulation, as opposed to the porcine model, which 'excels' in its relative paucity of natural collateral circulation and its resemblance to the human coronary circulation." Battler et al., *"Intracoronary Injection of Basic Fibroblast Growth Factor Enhances Angiogenesis in Infarcted Swine Myocardium,"* JACC, 22(7): 2001–6 (December 1993) at page 2002, col. 1. However, Battler et al., who administered bovine bFGF (i.e., FGF-2) to pigs in a myocardial infarct model, considered the varying results that are obtained from one animal species to another, and expressly discloses that the divergent results "thus emphasiz[e] the caution that must be exercised in extrapolating results from different animal models." Battler et al., at page 2005, col. 1. Further, Battler points out that "the dosage and mode of administration of bFGF [i.e., bovine FGF-2] may have profound implications for the biologic effect achieved." Battler, et al., at page 2005, col. 1. Thus, it is a further object of this invention to discover a dosage and a mode of administration of a fibroblast growth factor that would provide for the safe and efficacious treatment of CAD and/or post MI injury in a human patient. More generally, it is an object of the present invention to provide a pharmaceutical composition and method for inducing angiogenesis in a human heart.

SUMMARY OF THE INVENTION

The Applicants have discovered that a fibroblast growth factor, such as of SEQ ID NOS: 1–3, 5, 8–9, or 12–14 or an angiogenically active fragment or mutein thereof, when administered as a unit dose of about 0.2 $\mu$g/kg to about 36 $\mu$g/kg into one or more coronary vessels (IC) of a human patient in need of coronary angiogenesis, unexpectedly provides the human patient with a rapid and therapeutic cardiac angiogenesis sufficient to obviate surgical intervention and results in an unexpectedly superior increase in the treated patient's exercise tolerance time (ETT). By way of comparison, angioplasty is considered a therapeutic success if it provides an increase in a patient's ETT of greater than 30 seconds compared to the placebo. By the term "cardiac angiogenesis" or "coronary angiogenesis," as used herein, is meant the formation of new blood vessels, ranging in size from capillaries to arterioles which act as collaterals in coronary circulation.

FGFs that are suitable for use in the present invention include human FGF-1 (SEQ ID NO: 1), bovine FGF-1 (SEQ ID NO: 2), human FGF-2 (SEQ ID NO: 3), bovine FGF-2

(SEQ ID NO: 5), human FGF-4 (SEQ ID NO: 8), human FGF-5 (SEQ ID NO: 9), human FGF-6 (SEQ ID NO: 10), human FGF-8 (SEQ ID NO: 12), human FGF-9 (SEQ ID NO: 13) and human FGF-98 (SEQ ID NO: 14). In one embodiment, FGF molecules are human FGF-1 (SEQ ID NO: 1), bovine FGF-1 (SEQ ID NO: 2), human FGF-2 (SEQ ID NO: 3), bovine FGF-2 (SEQ ID NO: 5), human FGF-4 (SEQ ID NO: 8) and human FGF-5 (SEQ ID NO: 9). In an alternative embodiment, the FGF molecules are human FGF-6 (SEQ ID NO: 10), murine FGF-8 (SEQ ID NO: 12), human FGF-9 (SEQ ID NO: 13) or human FGF-98 (SEQ ID NO: 14).

Typically, the angiogenically active fragments of the present invention retain the distal two thirds of the mature FGF molecule (i.e., the two thirds of the molecule at the carboxy end that have the cell binding sites). For convenience, the terms "human FGF," "bovine FGF" and murine FGF are used herein in abbreviated form as "hFGF," "bFGF" and "mFGF," respectively.

The Applicants also discovered that a single unit dose of an FGF or an angiogenically active fragment thereof, when administered as a unit dose into one or more coronary vessels (IC) of a human patient in need of coronary angiogenesis (e.g., a human patient with coronary artery disease despite optional medical management), unexpectedly provides the human patient with a therapeutic benefit that is seen as early as two weeks after the single unit dose is administered (as reflected in symptoms), and that lasts at least 60 days after the single unit dose is administered (as reflected in ETT and the "Seattle Angina Questionnaire" (SAQ)). For example, when 28 human patients diagnosed as having CAD were assessed by the SAQ both before and 57 days after being administered IC a single unit dose of 0.33 $\mu$g/kg to 48 $\mu$g/kg of FGF-2 of SEQ ID NO: 5, the mean increase in their scores on the five criteria assessed ranged from 13 to 36 points, which is about 1.6–4.5 times greater than the 8 point change which was considered to be "clinically significant" in alternative modes of treatment. See Table 2. When the scores of the 15 first patients were broken down between those receiving a low dose (less than 2 $\mu$g/kg) and those receiving a higher dose (greater than or equal to 2 $\mu$g/kg) of FGF-2 of SEQ ID NO: 5, and assessed by the SAQ, both doses were found to provide scores that had "clinically significant" increases ranging from 12.3 to 58.1 and 10.9 to 32.1, respectively. Thus, whether the patients were administered the lower doses or the higher doses of the invention, their increased scores were about 1.4–7.2 times greater than the 8 point change which was considered to be "clinically significant" in alternative modes of treatment. See Table 3.

As part of this study, MRI was performed on 23 human patients diagnosed with CAD to assess ejection fraction, regional myocardial function and perfusion (delayed arrival zone). The patients were administered IC a single unit dose of 0.33 $\mu$g/kg to 12 $\mu$g/kg of FGF-2 of SEQ ID NO: 5. Their cardiac and coronary functions were objectively assessed by magnetic resonance imaging (MRI) both before and after treatment. The MRI results demonstrated significant improvement in regional wall motion (%) and wall thickening (%) during systole. The results also showed a significant reduction in the delayed arrival zone (% LV). The results did not demonstrate any significant change in ejection fraction (EF). Thus, the Applicants have demonstrated the clinical efficacy in humans of a single unit dose of an FGF when administered IC in accordance with the present invention.

Accordingly, in one aspect, the Applicants' invention is directed to a unit dose of FGF comprising a safe and therapeutically effective amount of an FGF of any one of SEQ ID NOS: 1–3, 5, 8–10 or 12–14 or an angiogenically active fragment or mutein thereof. Typically, the safe and therapeutically effective amount comprises about 0.2 $\mu$g/kg to about 36 $\mu$g/kg of an FGF of any one of SEQ ID NOS: 1–3, 5, 8–10 or 12–14 or an angiogenically active fragment or mutein thereof. In other embodiments, the safe and therapeutically effective amount of the unit dose comprises 0.2 $\mu$g/kg to 2.0 $\mu$g/kg, 2.0 $\mu$g/kg to 20 $\mu$g/kg or 20 $\mu$g/kg to 36 $\mu$g/kg of an FGF of any one of SEQ ID NOS: 1–3, 5, 8–10 or 12–14 or an angiogenically active fragment or mutein thereof. Expressed in absolute terms for the majority of human CAD patients, the unit dose of the present invention comprises 0.008 mg to 6.1 mg, more typically 0.3 mg to 3.5 mg, of the FGF of any one of SEQ ID NOS: 1–3, 5, 8–10 or 12–14 or an angiogenically active fragment or mutein thereof.

In another aspect, the present invention is directed to a pharmaceutical composition comprising a safe and therapeutically effective amount of an FGF or an angiogenically active fragment or mutein thereof, and a pharmaceutically acceptable carrier. Typically, the safe and therapeutically effective amount of an FGF comprises about 0.2 $\mu$g/kg to about 36 $\mu$g/kg of an FGF of any one of SEQ ID NOS: 1–3, 5, 8–10 or 12–14 or an angiogenically active fragment or mutein thereof, and a pharmaceutically acceptable carrier. In other embodiments of the pharmaceutical composition, the safe and therapeutically effective amount of an FGF comprises 0.2 $\mu$g/kg to 2 $\mu$g/kg, 2 $\mu$g/kg to 20 $\mu$g/kg or 20 $\mu$g/kg to 36 $\mu$g/kg of an FGF, such as an FGF of any one of SEQ ID NOS: 1–3, 5, 8–10 or 12–14 or an angiogenically active fragment or mutein thereof, and a pharmaceutically acceptable carrier.

In yet another aspect, the present invention is directed to a method of using the above described unit dose or pharmaceutical composition to treat a human patient for CAD or to induce coronary angiogenesis therein. The method comprises administering into one or more coronary vessels of a human patient in need of treatment for coronary artery disease (or in need of angiogenesis) a safe and therapeutically effective amount of a recombinant FGF or an angiogenically active fragment or mutein thereof. Typically, a portion of the safe and therapeutically effective amount is administered to each of two coronary vessels. More typically, the safe and therapeutically effective amount comprises about 0.2 $\mu$g/kg to about 36 $\mu$g/kg of an FGF of any one of SEQ ID NOS: 1–3, 5, 8–10 or 12–14 or an angiogenically active fragment or mutein thereof in a pharmaceutically acceptable carrier. In other embodiments, the safe and therapeutically effective amount comprises 0.2 $\mu$g/kg to 2 $\mu$g/kg, 2 $\mu$g/kg to 20 $\mu$g/kg or 20 $\mu$g/kg to 36 $\mu$g/kg of the FGF of any one of SEQ ID NOS: 1–3, 5, 8–10 or 12–14 or an angiogenically active fragment or mutein thereof in a pharmaceutically acceptable carrier.

Because FGF is a glycosoaminoglycan (e.g., heparin) binding protein and the presence of a glycosoaminoglycan (also known as a "proteoglycan" or a "mucopolysaccharide") optimizes activity and AUC, the IC dosages of the FGF of the present invention typically are administered within 20 minutes of the IV administration of a glycosoaminoglycan, such as a heparin.

Figure 1:
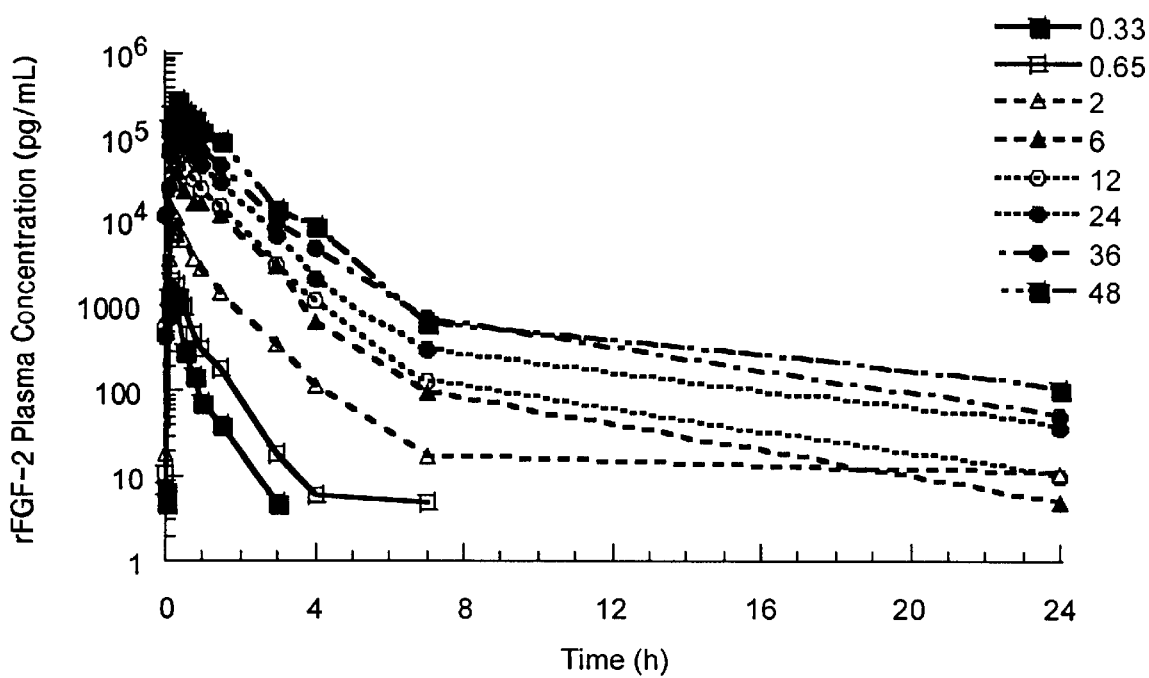
FIG. 1 is a plot of the mean rFGF-2 plasma concentration versus time (hours) for six different doses of rFGF-2 (SEQ ID NO: 5) administered by IC infusion in humans over a 20 minute period. The six doses of rFGF-2 in FIG. 1 are 0.33 μg/kg, 0.65 μg/kg, 2 μg/kg, 6 μg/kg, 12 μg/kg, and 24 μg/kg of lean body mass (LBM).
Figure 2:
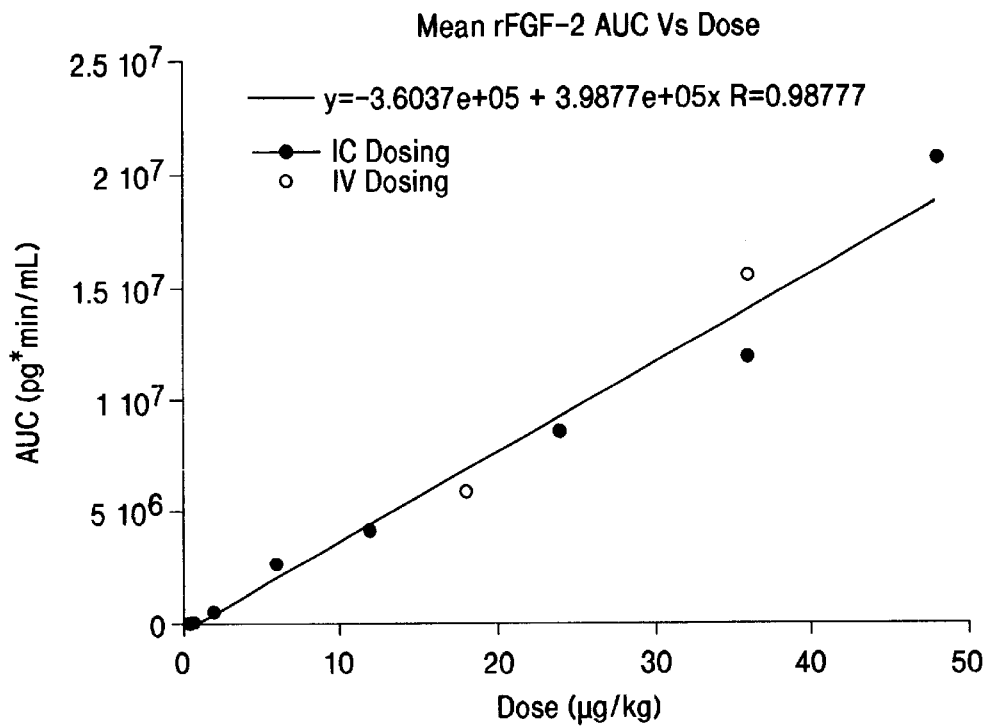

FIG. 2 is a plot of each individual patient's rFGF-2 area under the curve (AUC) in pg·hr/ml for FIG. 1 for the six doses of rFGF-2, and shows the dose linearity of systemic rFGF-2 exposure following IC infusion.

Figure 3:
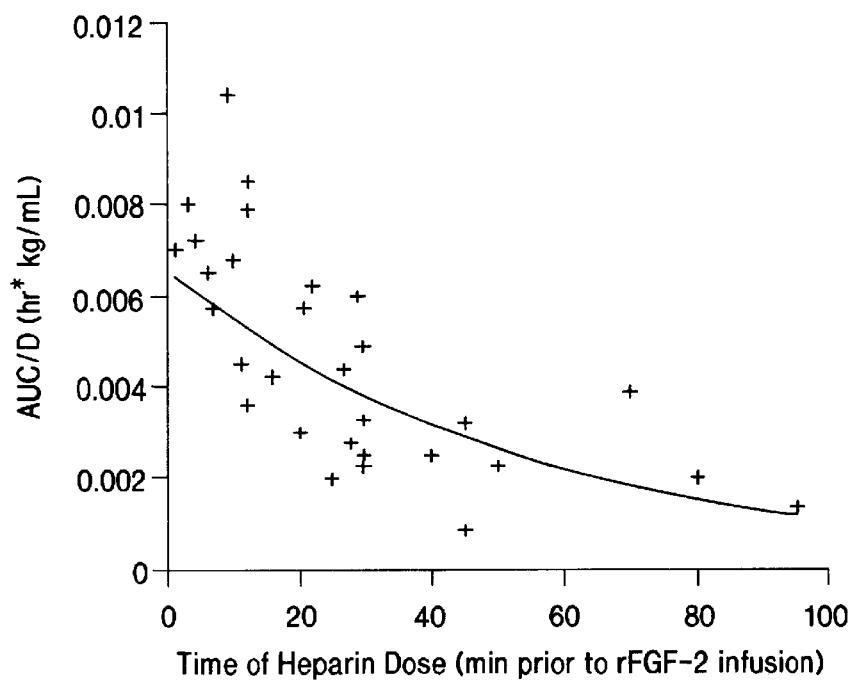

FIG. 3 is a plot individual human patient rFGF-2 dose normalized AUCs as a function of the time of heparin administration in "minutes prior to rFGF-2 infusion" and shows the influence of timing of heparin administration on rFGF-2 AUC.

DETAILED DESCRIPTION OF THE INVENTION

The Applicants have discovered that single dose of an FGF or an angiogenically active fragment or mutein thereof, when administered in a safe and therapeutically effective amount into one or more coronary vessels of a human patient diagnosed with CAD provides the patient with a safe and therapeutically efficacious treatment for the patient's coronary artery disease that lasts at least 6 months before a further treatment is needed. In fact, the Applicants' method for treating CAD, when assessed by the standard objective criterion employed in the art (i.e., ETT), provided an unexpectedly superior increase of one and a half to two minutes in the treated patient's ETT. This compares exceptionally well when compared to the increase of 30 seconds that is deemed clinically significant for the current mode of treatment, i.e., angioplasty.

By the phrase "safe and therapeutically effective amount" as used herein in relation to FGF is meant an amount of an FGF or an angiogenically active fragment or mutein thereof that when administered in accordance with this invention, is free from major complications that cannot be medically managed, and that provides for objective cardiac improvement in patients having symptoms of CAD despite optimum medical management. Thus, acute hypotension that can be managed by administration of fluids, with no other side effects is considered "safe" for the purpose of this invention. Typically, the safe and therapeutically effective amount of an FGF comprises about 0.2 μg/kg to about 36 μg/kg of the FGF of any one of SEQ ID NOS: 1–3, 5, 8–10 or 12–14 or an angiogenically active fragment or mutein thereof.

Accordingly, the present invention has multiple aspects. In its first aspect, the present invention is directed to a unit dose of the FGF medicament that has produced unexpectedly superior results in treating CAD in humans when compared to angioplasty. In particular, the unit dose comprises a safe and therapeutically effective amount of an FGF or an angiogenically active fragment or mutein thereof. Typically, the unit dose comprises about 0.2 μg/kg to about 36 μg/kg of the FGF of any one of SEQ ID NOS: 1–3, 5, 8–10 or 12–14 or an angiogenically active fragment or mutein thereof. In other embodiments of the unit dose, the safe and therapeutically effective amount comprises about 0.2 μg/kg to about 2 μg/kg, about 2 μg/kg to about 20 μg/kg or about 20 μg/kg to about 36 μg/kg of the FGF of any one of SEQ ID NOS: 1–3, 5, 8–10 or 12–14 or an angiogenically active fragment or mutein thereof. It is convenient to provide the unit dose of the present invention in a formulation comprising in absolute terms from 0.008 mg to 6.1 mg of the FGF of any one of SEQ ID NOS: 1–3, 5, 8–10 or 12–14 or an angiogenically active fragment or mutein thereof. In this embodiment, the unit dose contains a sufficient amount of FGF to accommodate dosing any one of the majority of CAD patients, ranging from the smallest patient (e.g., 40 kg) at the lowest dosage (about 0.2 μg/kg) through the larger patients (e.g., 170 kg) at about the highest dosage (about 36 μg/kg). More typically, the unit dose comprises 0.3 mg to 3.5 mg of the FGF of any one of SEQ ID NOS: 1–3, 5, 8–10 or 12–14 or an angiogenically active fragment or mutein thereof. The unit dose is typically provided in solution or lyophilized form containing the above referenced amount of FGF and an effective amount of one or more pharmaceutically acceptable buffers, stabilizers and/or other excipients as later described herein.

The active agent in the above described unit dose is a recombinant FGF or an angiogenically active fragment or mutein thereof. Typically, the active agent of the unit dose is the FGF of any one of SEQ ID NOS: 1–3, 5, 8–10 or 12–14. More typically, the active agent in the unit dose is hFGF-1 (SEQ ID NO: 1), bFGF-1 (SEQ ID NO: 2), hFGF-2 (SEQ ID NO: 3), bFGF-2 (SEQ ID NO: 5), hFGF-4 (SEQ ID NO: 8) or hFGF-5 (SEQ ID NO: 9). In an alternative embodiment, the active agent in the unit dose is hFGF-6 (SEQ ID NO: 10), mFGF-8 (SEQ ID NO: 12), hFGF-9 (SEQ ID NO: 13) or hFGF-98 (SEQ ID NO: 14).

The amino acid sequences and methods for making many of the mammalian FGFs that are employed in the unit dose, pharmaceutical composition and method of the present invention are well known in the art. In particular, references disclosing the amino acid sequence and recombinant expression of mammalian FGF 1-9 and FGF-98 are discussed sequentially below.

FGF-1: The amino acid sequence of hFGF-1 (SEQ ID NO: 1) and its recombinant expression are disclosed in U.S. Pat. No. 5,604,293 (Fiddes), entitled "Recombinant Human Basic Fibroblast Growth Factor," which issued on Feb. 18, 1997. See FIG. 2d of the '293 patent. This reference and all other references herein, whether cited before or after this sentence, are expressly incorporated herein by reference in their entirety. The amino acid sequence and recombinant expression of bFGF-1 (SEQ ID NO: 2) are also disclosed in U.S. Pat. No. 5,604,293 (Fiddes) which has been incorporated herein by reference. See, FIG. 1b of the '293 patent. Both hFGF-1 (SEQ ID NO: 1) and bFGF-1 (SEQ ID NO: 2) have 140 amino acid residues. bFGF-1 differs from hFGF-1 at 19 residue positions: 5(Pro→Leu), 21(His→Tyr), 31(Tyr→Val), 35(Arg→Lys), 40(Gln→Gly), 45(Gln→Phe), 47(Ser→Cys), 51(Tyr→Ile), 54(Tyr→Val), 64(Tyr→Phe), 80(Asn→Asp), 106(Asn→His), 109(Tyr→Val), 116(Ser→Arg), 117(Cys→Ser), 119(Arg→Leu), 120(Gly→Glu), 125(Tyr→Phe) and 137(Tyr→Val). In most instances, the differences are conserved. Further, the differences at residue positions 116 and 119 merely interchange the position of the Arg.

FGF-2: The amino acid sequence of hFGF-2 (SEQ ID NO: 3) and methods for its recombinant expression are disclosed in U.S. Pat. No. 5,439,818 (Fiddes) entitled "DNA Encoding Human Recombinant Basic Fibroblast Growth Factor," which issued on Aug. 8, 1995 (see FIG. 4 therein), and in U.S. Pat. No. 5,514,566 (Fiddes), entitled "Methods of Producing Recombinant Fibroblast Growth Factors," which issued on May 7, 1996 (see FIG. 4 therein). The amino acid sequence of bFGF-2 (SEQ ID NO: 5) and various methods for its recombinant expression are disclosed in U.S. Pat. No. 5,155,214, entitled "Basic Fibroblast Growth Factor," which issued on Oct. 13, 1992. When the 146 residue forms of hFGF-2 and bFGF-2 are compared, their amino acid sequences are nearly identical with only two residues that differ. In particular, in going from hFGF-2 to bFGF-2, the sole differences occur at residue positions 112(Thr→Ser) and 128(Ser→Pro).

FGF-3: FGF-3 (SEQ ID NO: 7) was first identified as an expression product of a mouse int-2 mammary tumor and its amino acid sequence is disclosed in Dickson et al., "*Potential Oncogene Product Related to Growth Factors*," Nature 326:833 (Apr. 30, 1987). FGF-3 (SEQ ID NO: 7), which has 243 residues when the N-terminal Met is excluded, is substantially longer than both FGF-1 (human and bovine) and FGF-2 (human and bovine). A comparison of amino acid residues for mFGF-3 (SEQ ID NO: 7) relative to bFGF-1 (SEQ ID NO: 2) and bFGF-2 (SEQ ID NO: 5) is presented in overlap fashion in Dickson, et al. (1987). When the amino acid sequence of mFGF-3 (SEQ ID NO: 7) is compared to bFGF-1 (SEQ ID NO 2): and bFGF-2 (SEQ ID NO: 5), FGF-3 has 5 locations containing residue inserts relative to both FGF-1 and FGF-2. The most significant of these inserts is a 12 and 14 residue insert relative to FGF-2 and FGF-1, respectively, beginning at residue position 135 of FGF-3. Allowing for the inserts, Dickson discloses that mFGF-3 has 53 residue identities relative to FGF-1 and 69 residue identities relative to FGF-2. In addition, FGF-3 contains a hydrophobic N-terminal extension of 10 residues relative to the N-terminus of the signal sequence in both FGF-1 and FGF-2. Relative to the C-terminus of bFGF-1 and bFGF-2, mFGF-3 contains an approximately 60 residue extension. It is unlikely that the C-terminal extension of mFGF-3 is necessary for activity. More likely, it is a moderator of activity by conferring receptor specificity on the FGF.

FGF-4: The amino acid sequence for the hst protein, now known as hFGF-4 (SEQ ID NO: 8), was first disclosed by Yoshida, et al., "*Genomic Sequence of hst, a Transforming Gene Encoding a Protein Homologous to Fibroblast Growth Factors and the int-2-Encoded Protein*," PNAS USA, 84:7305–7309 (October 1987). Including its leader sequence, hFGF-4 (SEQ ID NO: 8) has 206 amino acid residues. When the amino acid sequences of hFGF-4 (SEQ ID NO: 7), hFGF-1 (SEQ ID NO: 1), hFGF-2 (SEQ ID NO: 3) and mFGF-3 (SEQ ID NO: 7) are compared, residues 72–204 of hFGF-4 have 43% homology to hFGF-2 (SEQ ID NO: 5); residues 79–204 have 38% homology to hFGF-1 (SEQ ID NO: 1); and residues 72–174 have 40% homology to mFGF-3 (SEQ ID NO: 7). A comparison of these four sequences in overlap form is shown in Yoshida (1987) at FIG. 3. Further, the Cys at residue positions 88 and 155 of hFGF-4 are highly conserved among hFGF-1, hFGF-2, mFGF-3 and hFGF-4 and are found in a homologous region.

The two putative cell binding sites of hFGF-2 (SEQ ID NO: 3) occur at residue positions 36–39 and 77–81 thereof. See Yoshida (1987) at FIG. 3. The two putative heparin binding sites of hFGF-2 occur at residue positions 18–22 and 107–111 thereof. See Yoshida (1987) at FIG. 3. Given the substantial similarity between the amino acid sequences for human and bovine FGF-2, we would expect the cell binding sites for bFGF-2 (SEQ ID NO: 5) to also be at residue positions 36–39 and 77–81 thereof, and the heparin binding sites to be at residue positions 18–22 and 107–111 thereof. In relation to hFGF-1 (SEQ ID NO: 1), the putative cell binding sites occur at residues 27–30 and 69–72, and the putative heparin binding sites occur at residues 9–13 and 98–102. Insofar as bFGF-1 (SEQ ID NO: 2) has the identical amino acids at residue positions 9–13, 27–30, 69–72 and 98–102 as does hFGF-1 (SEQ ID NO: 1), bFGF-1 would be expected to have the same cell and heparin binding sites as does hFGF-1.

FGF-5: The amino acid sequence and method for cloning hFGF-5 (SEQ ID NO: 15) are disclosed in Zhan, et al., "*The Human FGF-5 Oncogene Encodes a Novel Protein Related to Fibroblast Growth Factors*," Molec. and Cell. Biol., 8(8):3487–3495 (August 1988). The Applicants also sequenced the FGF-5 and obtained the amino acid sequence of SEQ ID NO: 9, which differed from Zhan's sequence at residue position 236 (having a Lys instead of the Zhan's Asn) and at residue position 243 (having a Pro instead of Zhan's Ser). Both hFGF-5 (SEQ ID NO: 9) and hFGF-5 (SEQ ID NO: 15) have 266 amino acid residues that include a leader sequence of 67 residues upstream of the first residue of the FGF-2 of SEQ ID NO: 5 and a tail sequence that extends about 47 residues beyond the C-terminus of hFGF-2. A comparison between the amino acid sequences of hFGF-1 (SEQ ID NO: 1), hFGF-2 (SEQ ID NO: 3), mFGF-3 (SEQ ID NO: 7), hFGF-4 (SEQ ID NO: 8) and FGF-5 (SEQ ID NO: 9) is presented in FIG. 2 of Zhan (1988). In FIG. 2 of Zhan, hFGF-1, hFGF-2, mFGF-3 and hFGF-4 are identified as aFGF (i.e., acidic FGF), bFGF (i.e., basic FGF), int-2, and hstKS3, respectively, i.e., by their original names. In the above referenced comparison, two blocks of FGF-5 amino acid residues (90 to 180 and 187–207) showed substantial homology to FGF 1–4, i.e., 50.4% with FGF-4, 47.5% with FGF-3, 43.4% with FGF-2 and 40.2% with hFGF-1. See Zhan (1988) at FIG. 2. U.S. Pat. No. 5,155,217 (Goldfarb) and U.S. Pat. No. 5,238,916 (Goldfarb), which correspond to the Zhan publication, refer to the FGF-5 of Zhan as FGF-3. However, the art (as evidenced by Coulier below) has come to recognize that the hFGF of Zhan (and Goldfarb) as FGF-5 and not as FGF-3. The two Goldfarb patents contain the same amino acid sequence for hFGF-5 (SEQ ID NO: 15) as reported above by Zhan.

FGF-6: The amino acid sequence and method for cloning hFGF-6 (SEQ ID NO: 10) are disclosed in Coulier et al., "*Putative Structure of the FGF-6 Gene Product and Role of the Signal Peptide*," Oncogene 6:1437–1444 (1991). hFGF-6 is one of the largest of the FGFs, having 208 amino acid residues. When the amino acid sequences of human FGF-1, FGF-2, FGF-3, FGF-4, FGF-5, FGF-6 and FGF-7 are compared, there are strong similarities in the C-terminal two-thirds of the molecules (corresponding e.g., to residues 78–208 of hFGF-6 (SEQ ID NO: 10). In particular, 23 residues, including two cysteines (at positions 90–157 of hFGF-6 of SEQ ID NO: 10 were identical between the seven members of the family. This member increases to 33 residues when conserved amino acid residues are considered. The overall similarities between these seven human FGFs ranged from 32% to 70% identical residues and 48% to 79% conserved residues for the C-terminal two-thirds of the molecules. The sequence comparisons, relative to FGF-6, are shown in Table 1 herein.

TABLE 1

Amino Acid Sequence Comparison of hFGF-6 With Other hFGFs

|  | SEQ ID NO: | Identical Residues* | Conserved Residues** | Identical Residues* (%) | Conserved Residues** (%) |
|---|---|---|---|---|---|
| hFGF-4 | 8 | 91 | 103 | 70 | 79 |
| hFGF-5 | 9 | 64 | 82 | 49 | 63 |
| hFGF-3 | 7 | 55 | 78 | 42 | 60 |
| hFGF-2 | 3 | 54 | 69 | 42 | 53 |
| hFGF-7 | 11 | 47 | 68 | 36 | 52 |
| hFGF-1 | 1 | 42 | 62 | 32 | 48 |

*Number and percentages of identical or conserved residues were calculated for the C-terminal two-thirds of the hFGF6 molecule (residues 78–208).
**Conserved residues are defined according to the structure-genetic matrix of Feng et al., J. Mol. Evol., 21: 112–125 (1985).

Referring to Table 1, FGF-6 has the highest correspondence (91 identical residues/103 conserved residues) with FGF-4. This amounts to 70% identical and 79% conserved residues. hFGF-6 (SEQ ID NO: 10) differed most from hFGF-3 (SEQ ID NO: 2), hFGF-2 (SEQ ID NO: 3), hFGF-7 (SEQ ID NO: 11) and hFGF-1 (SEQ ID NO: 1), with 42, 42, 36 and 32; identical residues, respectively.

An overlayed comparison of the amino acid sequences of FGFs 1–7 is shown in FIG. 3 of incorporated Coulier (1991). FIG. 3 of Coulier shows that when in the C-terminal two thirds of the FGF molecules are aligned, there are 23 residue positions wherein the residues from all seven FGF members are identical. There are also ten residue positions wherein residues from all seven FGF members are conserved. Coulier (1991) at FIG. 3. In combination, these identical and conserved residues form about 6 locations of three to five residues on the terminal two thirds of each of the FGFs 1–7, wherein three to five residues are grouped together in all seven species of human FGF (i.e., hFGF 1–7).

FGF-7: The amino acid sequence of hFGF-7 (SEQ ID NO: 11) is disclosed in Miyamoto, et al., "*Molecular Cloning of a Novel Cytokine cDNA Encoding the Ninth Member of the Fibroblast Growth Factor Family, Which Has a Unique Secretion Property,*" Mol. and Cell. Biol. 13(7):4251–4259 (1993). In Miyamoto, the hFGF-7 was referred to by its older name KGF. As reflected in SEQ ID NO: 11, FGF-7 has 191 amino acid residues. Miyamoto compared hFGF-7 (SEQ ID NO: 11) to hFGF 1–6 and hFGF-9 shows that the carboxy terminal two thirds of the FGF-7 has comparable homology with the distal two thirds of the other members of the group. See Miyamoto (1993) at page 4254 (FIG. 2).

FGF-8: The amino acid sequence of mFGF-8 (SEQ ID NO: 12) and a method for its recombinant expression are disclosed in Tanaka et al., "*Cloning and Characterization of an Androgen-induced Growth Factor Essential for the Growth of Mouse Mammary Carcinoma Cells,*" PNAS USA, 89:8928–8932 (1992). The mFGF-8 of Tanaka has 215 amino acid residues. MacArthur, et al., "*FGF-8 isoforms activate receptor splice forms that are expressed in mesenchymal regions of mouse development,*" Development, 121:3603–3613 (1995) discloses that FGF-8 has 8 different isoforms that differ at the mature N-terminus but that are identical over the C-terminal region. The 8 isoforms arise because FGF-8 has 6 exons of which the first four (which correspond to the first exon of most other FGF genes) result in alternative splicing.

FGF-9: The amino acid sequence of hFGF-9 and a method for its recombinant expression are disclosed in Santos-Ocampo, et al., "*Expression and Biological Activity of Mouse Fibroblast Growth Factor,*" J. Biol. Chem., 271(3):1726–1731 (1996). Notwithstanding its title, Ocampo discloses the amino acid sequence of both hFGF-9 (SEQ ID NO: 13) and mFGF-9. Both the human and murine FGF-9 molecules have 208 amino acid residues and sequences that differ by only two residues. In particular, the hFGF-9 has Asn and Ser at residues 9 and 34, respectively, whereas the mFGF-9 has Ser and Asn, respectively. FGF-9 has complete preservation of the conserved amino acids that define the FGF family. Santos-Ocampo (1996) at page 1726. Half-maximal activation of FGF-9 is seen at 185 ng/ml heparin, whereas half-maximal activation of FGF-1 is seen at 670 ng/ml heparin. Santos-Ocampo (1996) at page 1730. When compared to FGF-1, both FGF-2 and FGF-9 require lower heparin concentrations for optimal activity.

FGF-98: The amino acid sequence of hFGF-98 (SEQ ID NO: 14) and a method for its recombinant expression are disclosed in provisional patent application Serial No. 60/083,553 which is hereby incorporated herein by reference in its entirety. hFGF-98, which is also known as hFGF-18, has 207 amino acid residues. Thus, hFGF-6 (207 residues), hFGF-9 (208 residues) and hFGF-98 (207 residues) are similar in size.

FGFs differentially bind to and activate one or more of four related transmembrane receptors which in turn mediate a biological response. The FGF receptors ("FGFR") are members of the tyrosine kinase receptor superfamily. The extracellular domain of the FGFR comprises 2–3 immunoglobulin-like ("IG-like") domains that are differentially expressed as a result of alternative splicing. Another alternative splicing event can also alter the sequence of the carboxy-terminal half of the Ig-like domain III without altering the reading frame. Santos-Ocampo (1996). The two splice forms, which are referred to as "b" and "c", occur for FGFRs 1, 2, 3 but not 4. A more detailed description of the FGFR is found in Mathieu, et al, "*Receptor Binding and Mitogenic Properties of Mouse Fibroblast Growth Factor 3,*" J. Biol. Chem., 270(41):24197–24203 (1995). The ability of FGF 1–9 to differentially stimulate FGFRs was receptor dependent as reported by Ornitz et al., J. Biol. Chem., 271(25):15292–15297 (1996). In Ornitz, the cell line BaF3 was divided into fractions and each fraction was transfected to express one of the following FGF receptors: FGFR1b, FGFR1c, FGFR2b, FGFR2c, FGFR3b, FGFR3c and FGF4 (minus one Ig-like domain). Thereafter, the transformed cell lines were exposed to one of FGF 1–9 (5 nM) and heparin (2 µg/ml) as a cofactor. The mitogenic response was then measured by incorporation of [$^3$H] thymidine. The results in cpm are as follows:

1. FGFR1b: similar mitogenic responses were produced by hFGF-1 (32,000 cpm) and hFGF-2 (28,000 cpm) with the next highest responses by mFGF-3 (about 16,000 cpm) and hFGF-4 (15,000 cpm);
2. FGFR1c: similar mitogenic responses were produced by hFGF-1, hFGF-2, hFGF-4, hFGF-5, and hFGF-6 (about 36,000 cpm), with mFGF-9 producing the only other significant response (about 19,000 cpm);
3. FGFR2b: best mitogenic responses were by hFGF-7 (14,000 cpm), hFGF-1 (12,500 cpm) and mFGF-3 (9,500 cpm);
4. FGFR2c: best mitogenic responses were by hFGF-4 (21,000 cpm), mFGF-9 (20,000 cpm), hFGF-6 (16,500 cpm), hFGF-1 (16,000 cpm), hFGF-2 (14,500 cpm), hFGF-5 (9,500 cpm), and mFGF-8 (9,000 cpm);
5. FGFR3b: mitogenic responses only by hFGF-1 (37,000 cpm) and mFGF-9 (26,000 cpm);
6. FGFR3c: best mitogenic responses by hFGF-1 (39,000 cpm), hFGF-2 (34,000 cpm), hFGF-4 (33,000 cpm), mFGF-8 (32,500 cpm), mFGF-9 (31,000 cpm), hFGF-5 (16,000 cpm) and hFGF-6 (13,000 cpm);
7. FGFR4Δ: best mitogenic responses by hFGF-2 (29,000 cpm), hFGF-4 and hFGF-6 (27,000 cpm), mFGF-8 (25,000 cpm), mFGF-1 (24,000 cpm), and hFGF-9 (20,000 cpm) with all others being 6,000 cpm or less.

As reflected above, only FGF-1 induces a significant mitogenic response in all of the receptors tested. Thus, FGF-1 can be thought of as a universal ligand with N- and C-terminal additions to the molecule giving rise to receptor specificity associated with the other FGF. Given the potential for diverse responses in vivo by systemically administered FGF, the present invention minimizes the potential for systemic responses by localized administration, and by discovering the appropriate dosage for the localized administration, i.e., by administering a therapeutically effective amount of a mammalian FGF into at least one coronary artery of a patient in need of treatment for CAD.

In the Examples that follow, bFGF-2 (SEQ ID NO: 5) was administered in vivo to rats, pigs and humans, and tested for angiogenic activity. The bFGF-2 of the Examples was made as described in U.S. Pat. No. 5,155,214. In the '214 patent, a DNA of SEQ ID NO: 4, which encodes a bFGF (hereinafter "FGF-2") of SEQ ID NO: 5, is inserted into a cloning vector, such as pBR322, pMB9, Col E1, pCRI, RP4 or λ-phage, and the cloning vector is used to transform either a eukaryotic or prokaryotic cell, wherein the transformed cell expresses the FGF-2. In one embodiment, the host cell is a yeast cell, such as *Saccharomyces cerevisiae*. The resulting full length FGF-2 that is expressed has 146 amino acids in accordance with SEQ ID NO: 5. Although the FGF-2 of SEQ ID NO: 5 has four cysteines, i.e., at residue positions 25, 69, 87 and 92, there are no internal disulfide linkages. ['214 at col. 6, lines 59–61.] However, in the event that cross-linking occurred under oxidative conditions, it would likely occur between the residues at positions 25 and 69.

The mammalian FGF-2 of SEQ ID NO: 5, which is of bovine origin, like the corresponding human FGF-2 is initially synthesized in vivo as a polypeptide having 155 amino acid residues. Abraham et al. *"Human Basic Fibroblast Growth Factor: Nucleotide Sequence and Genomic Organization,"* EMBO J., 5(10):2523–2528 (1986). When compared to the full length 155 residue bovine FGF-2 of Abraham, Applicants' FGF-2 of SEQ ID NO: 5 lacks the first nine amino acid residues, Met Ala Ala Gly Ser Ile Thr Thr Leu (SEQ ID NO: 6), at the N-terminus of the corresponding full length molecule. As discussed above, the FGF-2 of SEQ ID NO: 5 differs from human FGF-2 in two residue positions. In particular, the amino acids at residue positions 112 and 128 of the bFGF-2 of SEQ ID NO: 5 are Ser and Pro, respectively, whereas in hFGF-2, they are Thr and Ser, respectively. Given this substantial structural identity, the in vivo clinical results provided in the Examples and discussed elsewhere herein on bFGF-2 (SEQ ID NO: 5) should be directly applicable to hFGF-2 (SEQ ID NO: 3).

The recombinant bFGF-2 (SEQ ID NO: 5) of the Examples was purified to pharmaceutical quality (98% or greater purity) using the techniques described in detail in U.S. Pat. No. 4,956,455, entitled "Bovine Fibroblast Growth Factor" which issued on Sep. 11, 1990 and which was incorporated herein by reference in its entirety. In particular, the first two steps employed in the purification of the recombinant bFGF-2 of Applicants' unit dose are "conventional ion-exchange and reverse phase HPLC purification steps as described previously." [U.S. Pat. No. 4,956,455, citing to Bolen et al., PNAS USA 81:5364–5368 (1984).] The third step, which the '455 patent refers to as the "key purification step" ['455 at col. 7, lines 5–6], is heparin-SEPHAROSE® affinity chromatography, wherein the strong heparin binding affinity of the FGF-2 is utilized to achieve several thousand-fold purification when eluting at approximately 1.4M and 1.95M NaCl ['455 at col. 9, lines 20–25]. Polypeptide homogeneity was confirmed by reverse-phase high pressure liquid chromatography (RP-HPLC). Buffer exchange was achieved by SEPHADEX® G-25(M) gel filtration chromatography.

In addition to the mammalian FGF of any one of SEQ ID NOS: 1–3, 5, 8–10 or 12–14, the active agent in the unit dose of the present invention also comprises an "angiogenically active fragment thereof." By the term "angiogenically active fragment thereof" is meant a fragment of any one of the FGF of SEQ ID NOS: 1–3, 5, 8–10 or 12–14 that has about 80% of the residues sequence of SEQ ID NO: 5 and that retains the angiogenic effect of the corresponding mature mammalian FGF. A common truncation, is the removal of the N-terminal methionine, using well known techniques such as treatment with a methionine aminopeptidase. A second desirable truncation comprises the mammalian FGF without its leader sequence. Those skilled in the art recognize the leader sequence as the series of hydrophobic residues at the N-terminus of a protein that facilitate its passage through a cell membrane but that are not necessary for activity and that are not found on the mature protein.

Preferred truncations are determined relative to hFGF-2 (or the analogous bFGF-2). As a general rule, the amino acid sequence of a mammalian FGF is aligned with FGF-2 to obtain maximum homology. Portions of the mammalian FGF that extend beyond the corresponding N-terminus of the aligned FGF-2 (SEQ ID NO: 3 or 5) are suitable for deletion without adverse effect. Likewise, portions of the mammalian FGF that extend beyond the C-terminus of the aligned FGF-2 (SEQ ID NO: 3 or 5) are also capable of being deleted without adverse effect.

Fragments of FGF that are smaller than those described above are also within the scope of the present invention so long as they retain the cell binding portions of FGF and at least one heparin binding segment. As already discussed above, the heparin binding segments of FGF-2 (human or bovine) occur at residues 18–22 and 107–111, whereas the cell binding portions occur at residues 36–39 and 77–81. For example, it is well known in the art that N-terminal truncations of bFGF-2 do not eliminate its angiogenic activity in cows. In particular, the art discloses several naturally occurring and biologically active fragments of bFGF-2 of SEQ ID NO: 5 that have N-terminal truncations relative to the bFGF-2 of SEQ ID NO: 5. An active and truncated bFGF-2 having residues 12–146 of SEQ ID NO: 5 was found in bovine liver and another active and truncated bFGF-2, having residues 16–146 of SEQ ID NO: 5 was found in the bovine kidney, adrenal glands and testes. [See U.S. Pat. No. 5,155,214 at col. 6, lines 41–46, citing to Ueno, et al., Biochem and Biophys Res. Comm., 138:580–588 (1986).] Likewise, other fragments of the bFGF-2 of SEQ ID NO: 5 that are known to have FGF activity are FGF-2 (24–120)-OH and FGF-2 (30–110)-NH$_2$. [U.S. Pat. No. 5,155,214 at col. 6, lines 48–52.] These latter fragments retain both of the cell binding portions of bFGF-2 (SEQ ID NO: 5) and one of the heparin binding segments (residues 107–111). Accordingly, the angiogenically active fragments of a mammalian FGF typically encompass those terminally truncated fragments of a mammalian FGF that when aligned to an FGF-2 to maximize homology, have at least residues that correspond to residues 30–110 of bFGF-2 of SEQ ID NO: 5 (or the hFGF-2 of SEQ ID NO: 3); more typically, at least residues that correspond to residues 18–146 of bFGF-2 of SEQ ID NO: 5.

The unit dose of the present invention also comprises an "angiogenically active . . . mutein" of the mammalian FGF of any one of SEQ ID NOS: 1–3, 5, 8–10 or 12–14. By the term "angiogenically active . . . mutein" is meant a mutated form of the mammalian FGF of any one of SEQ ID NOS: 1–3, 5, 8–10 or 12–14 that structurally retains at least 80%, preferably 90%, of the residues of any one of SEQ ID NOS: 1–3, 5, 8–10 or 12–14 in their respective positions, and that functionally retains the angiogenic activity of the FGF of any one of SEQ ID NOS: 1–3, 5, 8–10 or 12–14. Preferably, the mutations are "conservative substitutions" using L-amino acids, wherein one amino acid is replaced by another biologically similar amino acid. Examples of conservative substitutions include the substitution of one hydrophobic residue such as Ile, Val, Leu, Pro, or Gly for another, or Phe⇋Tyr, Ser⇋Thr, or the substitution of one polar residue for another, such as between Arg and Lys, between Glu and Asp, or between Gln and Asn, and the like. Generally, the charged amino acids are considered interchangeable with one another. However, to make the substitution more conservative, one takes into account both the size and the likeness of the charge, if any, on the side chain. Other suitable substitutions include the substitution of serine for one or both of the cysteines at residue positions which are not involved in disulfide formation, such as residues 87 and 92 in hFGF-2 (SEQ ID NO: 3) or bFGF-2 (SEQ ID NO: 5). Preferably, substitutions are introduced at the N-terminus, which is not associated with angiogenic activity. However, as discussed above, conservative substitutions are suitable for introduction throughout the molecule.

One skilled in the art, using art known techniques, is able to make one or more point mutations in the DNA encoding a mammalian FGF of any one of SEQ ID NOS: 1–3, 5, 8–10 or 12–14 to obtain expression of an FGF polypeptide mutein (or fragment mutein) having angiogenic activity for use within the unit dose, compositions and method of the present invention. To prepare an angiogenically active mutein of the FGF of any one of SEQ ID NOS: 1–3, 5, 8–10 or 12–14, one uses standard techniques for site directed mutagenesis, as known in the art and/or as taught in Gilman, et al., Gene, 8:81 (1979) or Roberts, et al., Nature, 328:731 (1987), to introduce one or more point mutations into the cDNA that encodes the FGF of any one of SEQ ID NOS: 1–3, 5, 8–10 or 12–14.

In a second aspect, the present invention is directed to a pharmaceutical composition comprising a safe and an angiogenically effective dose of a mammalian FGF of any one of SEQ ID NOS: 1–3, 5, 8–10 or 12–14 or an angiogenically active fragment or mutein thereof, and a pharmaceutically acceptable carrier. Typically, the safe and angiogenically effective dose of the pharmaceutical composition of the present invention is in a form and a size suitable for administration to a human patient and comprises (i) 0.2 µg/kg to 36 µg/kg of an FGF of any one of SEQ ID NOS: 1–3, 5, 8–10 or 12–14 or an angiogenically active fragment or mutein thereof, (ii) and a pharmaceutically acceptable carrier. In other embodiments, the safe and angiogenically effective dose comprises 0.2 µg/kg to 2 µg/kg, 2 µg/kg to 20 µg/kg or 20 µg/kg to 36 µg/kg of the FGF of any one of SEQ ID NOS: 1–3, 5, 8–10 or 12–14 or an angiogenically active fragment or mutein thereof, and a pharmaceutically acceptable carrier.

By the term "pharmaceutically acceptable carrier" as used herein is meant any of the carriers or diluents known in the art for the stabilization and/or administration of a proteinaceous medicament, such as the mammalian FGF of any one of SEQ ID NOS: 1–3, 5, 8–10 or 12–14 disclosed herein, that does not itself induce the production of antibodies harmful to the individual receiving the composition, and which may be administered without undue toxicity. Within another aspect of the invention, pharmaceutical compositions are provided, comprising a recombinant FGF of any one of SEQ ID NOS: 1–3, 5, 8–10 or 12–14 or an angiogenically active fragment or mutein thereof in combination with a pharmaceutically acceptable carrier or diluent. Such pharmaceutical compositions may be prepared either as a liquid solution, or as a solid form (e.g., lyophilized) which is dissolved in a solution prior to administration. In addition, the composition may be prepared with suitable carriers or diluents for IC injection or administration. Pharmaceutically acceptable carriers or diluents are nontoxic to a human recipient at the dosages and concentrations employed. Representative examples of suitable carriers or diluents for injectable or infusible solutions include sterile water or isotonic saline solutions, which are preferably buffered at a suitable pH (such as phosphate-buffered saline or Tris-buffered saline), and optionally contain mannitol, dextrose, glycerol, ethanol, and/or one or more polypeptides or proteins such as human serum albumin (HSA). Stabilizers, such as trehalose, thioglycerol and dithiothreitol (DTT), may also be added.

A typical pharmaceutical composition comprises 0.001 to 10 mg/ml, more typically 0.03 to 0.5 mg/ml, of a rFGF of any one of SEQ ID NOS: 1–3, 5, 8–10 or 12–14 or an angiogenically active fragment or mutein thereof, 10 mM thioglycerol, 135 mM NaCl, 10 mM Na citrate, and 1 mM EDTA, pH 5. A suitable diluent or flushing agent for the above described composition is any of the above describe carriers. Typically, the diluent is the carrier solution itself comprising 10 mM thioglycerol, 135 mM NaCl, 10 mM Na citrate and 1 mM EDTA, pH5. The rFGF of any one of SEQ ID NOS: 1–3, 5, 8–10 or 12–14 or an angiogenically active fragment or mutein thereof is unstable for long periods of time in liquid form. To maximize stability and shelf life, the pharmaceutical composition of the present invention comprising an effective amount of rFGF any one of SEQ ID NOS: 1–3, 5, 8–10 or 12–14 or an angiogenically fragment or mutein thereof, in a pharmaceutically acceptable aqueous carrier should be stored frozen at −60° C. When thawed, the solution is stable for 6 months at refrigerated conditions. A typical unit dose would comprise about 5–10 ml of the above described composition having 1.5–8 mg of the FGF of any one of SEQ ID NOS: 1–3, 5, 8–10 or 12–14.

In another embodiment, the pharmaceutical composition comprises a unit dose of FGF of any one of SEQ ID NOS: 1–3, 5, 8–10 or 12–14 or an antigenically active fragment or mutein thereof in lyophilized (freeze-dried) form. In this form, the unit dose of FGF would be capable of being stored at refrigerated temperatures for substantially longer than 6 months without loss of therapeutic effectiveness. Lyophilization is accomplished by the rapid freeze drying under reduced pressure of a plurality of vials, each containing a unit dose of the FGF of the present invention therein. Lyophilizers, which perform the above described lyophilization, are commercially available and readily operable by those skilled in the art. Prior to administration to a patient, the lyophilized product is reconstituted to a known concentration, preferably in its own vial, with an appropriate sterile aqueous diluent, typically 0.9% (or less) sterile saline solution, or a compatible sterile buffer, or even sterile deionized water. Depending upon the weight of the patient in kg, a single dose comprising from 0.2 µg/kg to 36 µg/kg of the FGF of any one of SEQ ID NOS: 1–3, 5, 8–10 or 12–14 or an angiogenically active fragment or mutein thereof is withdrawn from the vial as reconstituted product for administration to the patient. Thus, an average 70 kg man that is being dosed at 24 µg/kg, would have a sufficient volume of the reconstituted product withdrawn from the vial to receive an IC infusion of (70 kg×24 µg/kg) 1680 µg (i.e., 1.680 mg).

In its third aspect, the present invention is directed to a method for treating a patient in need of treatment for CAD or MI, using the above described unit dose or pharmaceutical composition to treat a human patient for coronary artery disease (CAD). In particular, the present invention is directed to a method for treating a human patient for coronary artery disease, comprising administering a safe and therapeutically effective amount of a recombinant FGF of any one of SEQ ID NOS: 1–3, 5, 8–10 or 12–14 or an angiogenically active fragment or mutein thereof to one or more, typically two, coronary vessels of a human patient in need of treatment for coronary artery disease. A preferred coronary vessel is the coronary artery, although grafted saphenous veins and grafted internal mammary arteries, as provided by coronary angioplasty, are also suitable.

The method of the present invention provides clinical treatment of the underlying condition (i.e., CAD or MI) and not merely a treatment of the symptoms, such as provided by nitrates. Typically, the safe and therapeutically effective amount of the method of the present invention comprises 0.2 µg/kg to 36 µg/kg of the FGF of any one of SEQ ID NOS: 1–3, 5, 8–10 or 12–14 or an angiogenically active fragment or mutein thereof in a pharmaceutically acceptable carrier. In other embodiments, the safe and therapeutically effective amount comprises 0.2 µg/kg to 2 µg/kg , 2 µg/kg to 20 µg/kg or 20 µg/kg to 36 µg/kg of the FGF of any one of SEQ ID NOS: 1–3, 5, 8–10 or 12–14 or an angiogenically fragment or mutein thereof in a pharmaceutically acceptable carrier. In absolute terms, the safe and therapeutically effective amount is about 0.008 mg to about 6.1 mg of the FGF of any one of SEQ ID NOS: 1–3, 5, 8–10 or 12–14 or an angiogenically fragment or mutein thereof; more typically, 0.3 mg to 3.5 mg of the FGF of any one of SEQ ID NOS: 1–3, 5, 8–10 or 12–14 or an angiogenically fragment or mutein thereof.

The therapeutically effective amount of the rFGF-2 of the present invention is administered to at least one coronary vessel of a human patient diagnosed with CAD, symptomatic despite optimal medical management, using standard cardiac catheterization techniques already known and used in the art for the intracoronary administration of medicaments, e.g., thrombolytics, streptokinase, or radioopaque dyes or magnetic particles used to visualize the coronary arteries. By way of example, a coronary catheter is inserted into an artery (e.g., femoral or subclavian) of the patient in need of treatment and the catheter is pushed forward, with visualization, until it is positioned in the appropriate coronary vessel of the patient to be treated. Using standard precautions for maintaining a clear line, the pharmaceutical composition in solution form is administered by infusing the unit dose substantially continuously over a period of 10 to 30 minutes. Although the pharmaceutical composition of the invention could be administered over a longer period of time, the Applicants perceive no benefit and a potentially increased risk of thrombosis in doing so. Typically, a portion (e.g., one half) of the unit dose is administered in a first coronary vessel. Then, the catheter is repositioned into a second secondary coronary vessel and the remainder of the unit dose is administered with flushing of the catheter. Using the above-described repositioning procedure, portions of the unit dose may be administered to a plurality of coronary vessels until the entire unit dose has been administered. After administration, the catheter is withdrawn using conventional art known protocols. Signs of coronary angiogenesis are apparent in a matter of days following IC administration of the unit dose. Therapeutic benefit is seen as early as two weeks following the IC FGF administration. Clinically significant improvement is readily demonstrable by objective criterion (ETT and/or SAQ) 30 days following IC administration of the unit dose. In certain patients with progressive CAD disease, it may be necessary or appropriate to administer a unit dose of the FGF, for example, every six months or annually, to overcome the progression of the CAD during that interim period.

One of the benefits of the method of the present invention is cardiac angiogenesis. Accordingly, in another aspect, the present invention is directed to a method for inducing angiogenesis in a heart of a human patient, comprising administering as a unit dose into one or more coronary vessels of a human patient in need of coronary angiogenesis about 0.2 µg/kg to about 36 µg/kg (or in absolute terms about 0.008 mg to about 6.1 mg) of a recombinant mammalian FGF of any one of SEQ ID NOS: 1–3, 5, 8–10 or 12–14 or an angiogenically active fragment or mutein thereof.

Fifty-two (52) human patients diagnosed with CAD, who satisfied the criteria of Example 2 herein, were administered a unit dose of 0.33 µg/kg to 48 µg/kg of the FGF-2 of SEQ ID NO: 5 by IC infusion over about a 20 minute period. The 52 treated patients were then assessed by the Seattle Angina Questionnaire, which provides an assessment based upon a mixed combination of objective and subjective criteria. See Table 2 The Seattle Angina Questionnaire is a validated, disease-specific instrument with the following five subscales that are assessed both before and after treatment: 1) "exertional capacity"=limitation of physical activity; 2) "disease perception"=worry about MI; 3) "treatment satisfaction"; 4) "angina frequency"=number of episodes and sublingual nitroglycerin usage; and 5) "angina stability"=number of episodes with most strenuous physical activity. The possible range for each of the five subscales is 0 to 100 with the higher scores indicating a better quality of life. Moreover, a mean change of 8 points or more between the mean baseline scores (before treatment) and the post-treatment scores is recognized as being "clinically significant." Table 2 reports that the 28 patients, who were pretested and then administered a single unit dose of 0.33 µg/kg to 24 µg/kg of the FGF-2 of SEQ ID NO: 5 by IC infusion, exhibited a mean score increase of 13 to 36 points for the five "quality of life" criteria assessed by the "Seattle Angina Questionnaire." See Table 2 herein. These 13 to 36 point increases were about 1.6 to 4.5 times greater than the 8 point change which is recognized in the art as being "clinically significant" in alternative modes of treatment. See Table 2 herein. Moreover, when the combined results for the first 15 patients of Table 2 were broken down between low dose (less than or equal to 2 µg/kg) and high (more than 2 µg/kg) doses of FGF-2 of SEQ ID NO: 5, and assessed by the "Seattle Angina Questionnaire," both doses were found to provide increased scores that ranged from about 12.3 to 58.1 and about 10.9 to 32.1, respectively. See Table 3 herein. The increased scores were about 1.4 to 7.2 times greater than the 8 point change which is considered to be "clinically significant" in alternative modes of treatment.

In the same Phase I trial, fifty two human patients who were diagnosed with CAD and who satisfied the criteria of Example 2 herein, were administered IC a single unit dose of 0.33 µg/kg to 48 µg/kg of FGF-2 of SEQ ID NO: 5. The maximum tolerated dose (MTD) in humans was defined as 36 µg/kg based upon the occurrence of severe but transient hypotension in 2/10 patients at 48 µg/kg. (In contrast, the MTD in pigs was defined as 6.5 µg/ml.) At one of the sites, the hearts of 23 human patients were assessed both before ("baseline") and 30 and 60 days after treatment by magnetic resonance imaging (MRI) for objective signs of improved coronary sufficiency. Among the objective criteria assessed by MRI are the following: 1) left ventricular (LV) ejection fraction (EF); 2) normal wall thickness (NWT); 3) normal wall motion (NWM); 4) collateral extent; 5) ischemic area zone; 6) targeted wall thickness (TWT); 7) targeted wall motion (TWM); and 8) perfusion or delayed arrival zone (%LV). The patients were also assessed for angina, treadmill exercise duration, rest/exercise nuclear perfusion. The results are summarized in Table

TABLE 2

COMPARISON OF QUALITY OF LIFE BEFORE AND 57 DAYS AFTER IC FGF-2

| Questionnaire (SAQ) Subscales | Baseline (Pre FGF-2) Mean Score ± SD | 57 Days Post FGF-2 Mean Score ± SD | Mean Change[1] | p Value | n |
|---|---|---|---|---|---|
| Exertional Capacity | 55 ± 23 | 68 ± 25 | 13* | 0.02 | 28 |
| Angina Frequency | 42 ± 32 | 66 ± 28 | 24* | <0.001 | 28 |
| Angina Stability | 46 ± 26 | 82 ± 20 | 36* | <0.001 | 27 |
| Disease Perception | 40 ± 21 | 61 ± 26 | 19* | <0.001 | 28 |
| Treatment Satisfaction | 74 ± 24 | 88 ± 16 | 14* | 0.002 | 28 |

*Significantly different from baseline to fifty-seven days.
[1]A mean change of 8 points or more is considered clinically significant.

4. Table 4 reflects that the baseline angina class decreased from 2.6 to 1.4 and 1.2 at 30 and 60 days, respectively post IC FGF-2. The mean treadmill exercise time increased from

TABLE 3

IMPROVEMENTS IN THE QUALITY OF LIFE AT DAY 57 (POST IC rFGF-2) AT LOWER AND HIGHER DOSES

| Seattle Angina Questionnaire (SAQ) Subscales | Dose < 2 µg/kg IC rFGF-2 (n = 7) Mean Change in Score (Day 57 score-screen score) | Dose > 2 µg/kg IC rFGF-2 (n = 8) Mean Change in Score (Day 57 score-screen score) | Independent Samples | t-test |
|---|---|---|---|---|
| Exertional Capacity | 12.30 (23.3) | 15.98 (28.7) | t = −.27 | p = .79 |
| Disease Perception | 26.19 (26.9) | 24.47 (21.2) | t = .14 | p = .89 |
| Treatment Satisfaction | 22.32 (27.7) | 10.93 (17.3) | t = .97 | p = .35 |
| Angina Frequency | 28.57 (27.3) | 13.75 (22.6) | t = 1.15 | p = .27 |
| Angina Stability | 58.13 (12.9) | 32.14 (34.5) | t = 1.75 | p = .108 |

1. Possible range for each subscale is 0 to 100 with higher scores indicating better quality of life.
2. Standard deviation noted in parentheses.

a baseline of 8.5 minutes to 9.4 and 10.0 minutes at 30 and 60 days, respectively, post treatment. No significant difference was observed in the left ventricular ejection fraction (LV EF). However, the target wall motion increased significantly, moving from a baseline of 15.4% to 23.5% (day 30) and 24.1% (day 60) post FGF-2 treatment. Likewise the target wall thickening increased significantly from a baseline of 28.7% to 34.7% (day 30) and 45.9% (day 60) post FGF-2 treatment. There was also a significant increase in perfusion, as measured by a decrease in the delayed arrival zone (%LV), with the delayed arrival zone decreasing from a baseline of 18.9% to 7.1% (day 30) and 1.82% (day 60) post FGF-2 treatment. Thus, providing CAD patients with a single IC infusion of FGF-2 in accordance with the present invention provided the patients with a significant physical improvement as objectively measured by MRI and other conventional criteria.

Pharmacokinetics and Metabolism

The molecular structure of FGF-2 contains a positively charged tail that is known to bind to proteoglycan chains (heparin and heparin-like structures) on cell surfaces and on the endothelial wall of the vasculature. See Moscatelli, et al., "*Interaction of Basic Fibroblast Growth Factor with Extracellular Matrix and Receptors,*" Ann. NY Acad. Sci., 638:177–181 (1981). Because the endothelium is responsible for binding FGF-2 and acts as a sink after injection, we believed that rFGF-2 will undergo a fast biodistribution phase right after administration. Accordingly, we targeted the intracoronary as opposed to the intravenous route of administration.

The kidneys and liver are the major organs for the elimination of rFGF-2. In particular, the kidneys have a protein cutoff of about 60 kD and thus retain serum albumin (MW 60 kD). However, the FGF-2 of SEQ ID NO: 5 has

TABLE 4

MEAN DATA AND DATA RESULTS AS A FUNCTION OF TIME AND DOSE

| | Baseline | 30 Day | 60 Day |
|---|---|---|---|
| Angina Class | 2.6 ± 0.7 | 1.4 ± 0.9*** | 1.2 ± 0.8*** |
| Exercise Time (min.) | 8.5 ± 2.6 | 9.4 ± 1.9*** | 10.0 ± 2.5** |
| LV EF (%) | 47.4 ± 12.3 | 47.4 ± 10.6 | 48.6 ± 11.0 |
| Target Wall Motion (%) | 15.4 ± 10.1 | 23.5 ± 12.0* | 24.1 ± 10.1** |
| Target Wall Thickening (%) | 28.7 ± 14.0 | 34.7 ± 14.1 | 45.9 ± 11.7** |
| Delayed Arrival Zone (% LV) | 18.9 ± 8.3 | 7.1 ± 3.6*** | 1.82 ± 2.4*** |

*= p < 0.05
**= p < 0.01
***= p < 0.001 (2-tailed, paired)

a molecular weight of about 16 kD. Accordingly, renal excretion is to be expected. In a radiolabelled biodistribution study of commercially available bovine FGF-2 (bFGF-2), both the liver and the kidney were shown to contain high counts of the radiolabelled bFGF-2 at 1 hour after IV or IC injection. In the same study, FGF-2 appeared to bind to red blood cells, however these results were not confirmed by in vitro analysis of the whole blood. In a published study, wherein another recombinant iodinated form of bFGF-2 was given to rats, the liver was identified as the major organ of elimination. Whalen et al., "*The Fate of Intravenously Administered bFGF and the Effect of Heparin,*" Growth Factors, 1:157–164 (1989). More particularly, it is known that FGF-2 binds in the general circulation to $\alpha_2$-macroglobulin and that this complex is internalized by receptors on the Kupffer cells. Whalen et al. (1989) and LaMarre et al., "Cytokine Binding and Clearance Properties of Proteinase-Activated Alpha-2-Macroglobulins," Lab. Invest., 65:3–14 (1991). Labelled FGF-2 fragments were not found in the plasma, but they were found in the urine and corresponded in size to intracellular breakdown products. When FGF-2 was administered in combination with heparin, the renal excretion of FGF-2 was increased. Whalen et al. (1989). The FGF-2 molecule, which is cationic when not complexed with heparin, is likely repelled by the cationic heparin sulfate of the glomerular basement membrane. The FGF-2/heparin complex is more neutrally charged, and therefore is more easily filtered and excreted by the kidney.

We determined the pharmacokinetics of rFGF-2 (SEQ ID NO: 5) after intravenous (IV) and intracoronary (IC) administration in domestic Yorkshire pigs, after IV dosing in Sprague Dawley ("SD") rats, and after IC administration in CAD human patients. In all species, the rFGF-2 plasma concentrations after IV and/or IC injection followed a biexponential curve with an initial steep slope and considerable decrease over several log scales (the distribution phase) during the first hour, followed by a more moderate decline (the elimination phase). FIG. 1 provides a plasma concentration versus time curve showing these phases in humans after IC administration of rFGF-2 of SEQ ID NO: 5 as a function of the following doses: 0.33 µg/kg, 0.65 µg/kg, 2 µg/kg, 6µg/kg, 12 µg/kg and 24 µg/kg of lean body mass (LBM). The plasma concentrations of rFGF-2 of SEQ ID NO: 5 were determined by a commercially available ELISA (R &D Systems, Minneapolis Minn.) that was marketed for analysis of human FGF-2. The ELISA assay showed 100% cross-reactivity with the rFGF-2 of SEQ ID NO: 5. Other members of the FGF family, as well as many other cytokines, were not detected by this assay. Further, heparin does not interfere with the assay.

The design of these pharmokinetic studies, pharmacokinetic parameters, and conclusions are listed in Tables 5 and 6 for studies in pigs and rats, respectively. The reader is referred to these tables for the specific details. However, among the points to be noted are that the half-life ($T_{1/2}$) was 2.8±0.8 to 3.5 hours following a single IC infusion for the single component model for animals having a clearance (CL) of 702±311 to 609±350 ml/hr/kg. The results of this study show that the pharmacokinetics of the recombinant bFGF-2 of SEQ ID NO: 5 were substantially identical regardless of whether the animals were dosed via the IC or IV routes. See Table 5. In pigs, the maximum tolerated dose of recombinant bFGF-2 was 6.5 µg/kg. Among the other pharmacokinetic results to be taken from Tables 5 and 6 of these studies is that there is a fast distribution phase followed by a more moderate elimination phase, and dose linearity as reported in FIG. 1 for humans. Also, there were no gender differences. Further, the three compartment model was analyzed for pigs receiving 70 U/kg of heparin approximately ("~") 15 minutes before receiving 0.65–6.5 µg/kg by 5–10 minute IC infusion. The half lives ($T_{1/2}\alpha$, $T_{1/2}\beta$, and $T_{1/2}\gamma$) for the three compartments were 1.5 minutes, 17 minutes, and 6.6 hours, respectively. In these animals, the initial volume ("$V_1$") was approximately the plasma volume, and the steady state volume ("$V_{ss}$") was approximately 10-fold the plasma volume. See Table 5. In pigs, the binding of recombinant bFGF-2 of SEQ ID NO: 5 to circulating heparin appears to decrease biodistribution and elimination. Likewise, in rats, both the volume of distribution and the clearance of rFGF-2 were smaller when heparin was administered. See Table 6. Further, the greatest and most favorable changes on clearance of FGF-2 were found when heparin was administered within ±15 minutes, preferably immediately prior to rFGF-2 IC infusion. See Table 6.

The pharmacokinetics of the rFGF-2 of SEQ ID NO: 5 was studied in humans, diagnosed with CAD despite optimal medical management, in a Phase 1 clinical study supporting this filing. The doses of rFGF-2 employed in that Phase 1 study were 0.33 µg/kg, 0.65 µg/kg, 2 µg/kg, 6µg/kg, 12 µg/kg, and 24 µg/kg of lean body mass (LBM), and all doses were administered by a 20 minute IC infusion (10 minutes into each of two patent coronary vessels) after pretreating the patient with 40 U/kg heparin which was administered IV or IC 1–95 minutes before rFGF-2 infusion. FIGS. 1–3 herein summarize the data underlying those results. In particular, FIG. 1 is a plot of the mean rFGF-2 plasma concentration versus time (hours) for the six different doses of rFGF-2 (SEQ ID NO: 5) administered by IC infusion as described above over a 20 minute period. FIG. 1 shows dose linearity and a biphasic plasma level decline, i.e., a fast distribution phase during the first hour, followed by an elimination phase with $T_{1/2}$ of 1.9±2.2 hours. The dose linearity is more readily seen in FIG. 2 which is a plot of the individual patient rFGF-2 area under the curve (AUC) in pg·hr/ml for FIG. 1 for each of the six doses of rFGF-2 administered. FIG. 3 is a plot individual human patient rFGF-2 dose normalized AUCs versus time of heparin dose in "minutes prior to rFGF-2 infusion" and shows the influence of timing of heparin administration on rFGF-2 AUC. FIG. 3 shows that the greatest AUC/dose was achieved when an effective amount of a glycosoaminoglycan, such as heparin, was preadministered within 30 minutes or less of IC rFGF-2 infusion, more preferably within 20 minutes or less of IC

TABLE 5

Pharmacokinetics (PK) and Pharmacodynamics of rFGF-2 in Pigs

| Animals | Dosing Regimen | PK Parameters | Results |
| --- | --- | --- | --- |
| Domestic Yorkshire pigs under general anesthesia (n = 13; 30 ± 5 kg) | 2–20 µg/kg IV bolus<br>2–20 µg/kg IC bolus<br>20 µg/kg by 10-min IC infusion<br>70 U/kg heparin ~ 15 min before rFGF-2 | CL = 702 ± 311 mL/hr/kg<br>T½ = 2.8 ± 0.8 hr. | Systemic PK identical between IV and IC route<br>Fast distribution phase<br>Dose-linearity<br>Transient decreases of MAP |
| Domestic Yorkshire pigs under general anesthesia (n = 17; 26 ± 4 kg) | 0.65–6.5 µg/kg by 5-min IC infusion<br>70 U/kg heparin ~ 15 min before rFGF-2 | CL = 609 ± 350 ml/hr/kg<br>T½ = ~3.5 hr<br>3-Comp. Model:<br>T½α = 1.5 min | No gender difference in PK<br>Biphasic decline of plasma rFGF-2<br>Dose-linearity<br>$V_1$ equal to ~ plasma volume |

TABLE 5-continued

Pharmacokinetics (PK) and Pharmacodynamics of rFGF-2 in Pigs

| Animals | Dosing Regimen | PK Parameters | Results |
|---|---|---|---|
| Domestic Yorkshire pigs under general anesthesia (n = 6; 25 ± 5 kg) | 6.5 μg/kg weekly by 5 min IV infusion for 6 weeks 70 U/kg heparin 10 min before rFGF-2 (n = 3), or rFGF-2 alone (n = 3) | $T\frac{1}{2}\beta$ = 17 min $T\frac{1}{2}\gamma$ = 6.6 hr CL = 580 ml/hr/kg $V_1$ = 55 ml/kg $V_{ss}$ = 523 ml/kg Without Heparin (Doses 1–6): $T\frac{1}{2}$ = 2–6 hr CL = 777–2749 ml/hr/kg $V_{ss}$ = 871–12,500 ml/kg With Heparin (Doses 1–6): $T\frac{1}{2}$ = 2–3 hr CL = 235–347 ml/hr/kg $V_{ss}$ = 71–153 ml/kg | $V_{ss}$ equal to ~ 10-fold plasma volume Magnitude and duration of MAP decrease correlated with rFGF-2 dose and peak plasma level The rFGF-2 distribution phase was less steep, the volume of distribution smaller, and clearance was slower with heparin-pretreatment Binding of rFGF-2 to circulating heparin appears to decrease biodistribution and elimination Both volume and clearance of rFGF-2 increased at later doses (potential receptor upregulation), but more so in the absence of heparin Magnitude and duration of MAP decreases were similar with or without heparin |

TABLE 6

Pharmacokinetics (PK) of rFGF-2 in Rats

| Animals | Dosing Regimen | PK Parameters | | | Results |
|---|---|---|---|---|---|
| Conscious SD rats (n = 18; 322 ± 93 g) | 3–100 μg/kg bolus IV injection | $T\frac{1}{2}$ = 1.1 ± 0.51 hr CL = 4480 ± 2700 ml/hr/kg $V_{ss}$ = 1924 ± 1254 ml/kg | | | Fast distribution phase Apparent dose-linearity |
| conscious SD rats (n = 54; 149 ± 12 g) | 30–300 μg/kg weekly by bolus IV injection for 6 weeks No heparin pretreatment | $T\frac{1}{2}$ = 1.4 ± 0.13 hr CL = 1691 ± 169 ml/hr/kg $V_{ss}$ = 1942 ± 358 ml/kg | | | Time-invariant PK; plasma profiles, PK parameters and AUCs were similar over time Dose-linearity |
| Conscious SD rats (27 males; 381 ± 48 g; 20 females; 268 ± 22 g) | 30 μg/kg bolus IV injection No heparin 40 U/kg IV Heparin: at ~15 min just prior to rFGF-2 at +15 min at +3 hr | Time-Average PK Parameters: $T\frac{1}{2}$ hr 0.75 0.91 1.3 1.2 0.93 | CL ml/hr/kg 4332 1728 516 1158 1338 | $V_{ss}$ ml/kg 2389 844 147 626 1351 | In all cases, heparin increased the rFGF-2 plasma levels Both volume of distribution and clearance of rFGF-2 were smaller with heparin Greatest changes on CL and $V_{ss}$ were observed when heparin was administered immediately prior to rFGF-2 | rFGF-2 infusion. Typically, an effective amount of a glycosoaminoglycan is 40–70 U/kg heparin. These pharmacokinetic results are summarized in Table 7 herein.

The rFGF-2 distribution phase was less steep with heparin, the volume of distribution smaller, and the clearance slower, as compared to rFGF-2 without heparin. It appears that the complex of rFGF-2 with circulating heparin decreases the biodistribution and elimination of rFGF-2. Although the binding of FGF-2 to heparin-like structures is strong (dissociation constant ~$2\times10^{-9}$ M), the binding of FGF-2 to the FGF-2 receptor is approximately two orders of magnitude higher (dissociation constant ~$2\times10^{-11}$ M). Moscatelli et al., (1991). In addition, the complexation of the rFGF-2 of SEQ ID NO: 5 with a glycosoaminoglycan, such as a heparin, might increase signal transduction and mitogenesis, and/or protect the rFGF-2 from enzymatic degradation.

The examples, which follow, provide more details on the selection criterion and the Phase I clinical trial that gave rise to the data discussed above.

EXAMPLE 1

"Unit Dose of rFGF-2 Employed in the Phase I Clinical Trial"

The rFGF-2 of SEQ ID NO: 5 was formulated as a unit dose and pharmaceutical composition and administered to rats, pigs and ultimately to humans in the Phase I clinical trial referenced herein. The various formulations are described below.

The rFGF-2 Unit Dose was provided as a liquid in 3 cc type I glass vials with a laminated gray butyl rubber stopper and red flip-off overseal. The rFGF-2 unit dose contained 1.2 ml of 0.3 mg/ml rFGF-2 of SEQ ID NO: 5 in 10 mM sodium citrate, 10 mM monothioglycerol, 1 mM disodium dihydrate EDTA (molecular weight 372.2), 135 mM sodium chloride, pH 5.0. Thus, in absolute terms, each

TABLE 7

Pharmacokinetics of rFGF-2 in Human

| Subjects | Dosing Regimen | PK Parameters | Results |
|---|---|---|---|
| Patients with CAD | 0.33–24 µg/kg LBM* by 20-min IC injection (10 min in left main coronary artery + 10 min in right main coronary artery) 0.33 µg/kg, n = 4 0.65 µg/kg, n = 4 2 µg/kg, n = 8 6 µg/kg, n = 4 12 µg/kg, n = 4 24 µg/kg, n = 8 36 µg/kg, n = 10 48 µg/kg, n = 10 40 U/kg heparin pretreatment, 1–95 min before rFGF-2 infusion | Preliminary PK data from 0.33–24 µg/kg doses (n = 32) $T\frac{1}{2}$ = 1.9 ± 2.2 hr CL = 264 ± 150 ml/hr/kg $V_{ss}$ = 184 ± 74 ml/kg | Biphasic plasma level decline: fast distribution phase during 1 hr; followed by elimination phase with $T\frac{1}{2}$ approximately (~) 2 hr Dose-linearity Greater rFGF-2 exposure (as measured by the AUC) was found when heparin pretreatment was given closer to the start of the rFGF-2 infusion, preferably within 20 minutes |

*LBM = lean body mass vial (and unit dose) contained 0.36 mg rFGF-2. The vials containing the unit dose in liquid form were stored at 2° to 8° C.

The rFGF diluent was supplied in 5 cc type I glass vials with a laminated gray butyl rubber stopper and red flip-off overseal. The rFGF-2 diluent contains 10 mM sodium citrate, 10 mM monothioglycerol, 135 mM sodium chloride, pH 5.0. Each vial contained 5.2 ml of rFGF-2 diluent solution that was stored at 2° to 8° C.

The rFGF-2 Pharmaceutical Composition that was infused was prepared by diluting the rFGF-2 unit dose with the rFGF diluent such that the infusion volume is 10 ml. In order to keep the EDTA concentration below the limit of 100 µg/ml, the total infusion volume was increased to 20 ml when proportionately higher absolute amounts of FGF-2 were administered to patients with high body weights.

EXAMPLE 2

"Selection Criteria for Patients with Coronary Artery Disease for Treatment with rFGF-2"

The following selection criteria were applied to Phase I patients with coronary artery disease, whose activities were limited by coronary ischemia despite optimal medical management, and who were not candidates for approved revascularization therapies:

Inclusion criteria: Subject is eligible if:
Male or female, greater than or equal to 18 years of age
Diagnosis of coronary artery disease (CAD)
Suboptimal candidates for approved revascularization procedures, e.g., angioplasty, stents, coronary artery bypass graft (CABG) (or refuses those interventions)
Able to exercise at least three minutes using a modified Bruce protocol and limited by coronary ischemia
Inducible and reversible defect of at least 20% myocardium on pharmacologically stressed thallium sestamibi scan
CBC, platelets, serum chemistry within clinically acceptable range for required cardiac catheterization
Normal INR, or if anticoagulated with Coumadin, INR<2.0
Willing and able to give written informed consent to participate in this study, including all required study procedures and follow-up visits Exclusion criteria: Subject is not eligible if:
Malignancy: any history of malignancy within past ten years, with the exception of curatively treated basal cell carcinoma.
Ocular conditions: proliferative retinopathy, severe non-proliferative retinopathy, retinal vein occlusion, Eales' disease, or macular edema or funduscopy by ophthalmologist: history of intraocular surgery within six months
Renal function: creatinine clearance below normal range adjusted for age; protein>250 mg or microalbumin>30 mg/24 h urine
Class IV heart failure (New York Heart Association)
Ejection fraction<20% by echocardiogram, thallium scan, MRI or gated pooled blood scan (MUGA)
Hemodynamically relevant arrhythmias (e.g., ventricular fibrillation, sustained ventricular tachycardia)
Severe valvular stenosis (aortic area<1.0 $cm^2$, mitral area<1.2 $cm^2$), or severe valvular insufficiency
Marked increase in angina or unstable angina within three weeks
History of myocardial infarction (MI) within three months
History of transient ischemic attack (TIA) or stroke within six months
History of CABG, angioplasty or stent within six months
History of treatment with transmyocardial laser revascularization, rFGF-2, or vascular enodothelial growth factor (VEGF) within six months
Females of child-bearing potential or nursing mothers
Any pathological fibrosis, e.g., pulmonary fibrosis, scleroderma
Known vascular malformation, e.g., AV malformation, hemangiomas
Coexistence of any disease which might interfere with assessment of symptoms of CAD, e.g., pericarditis, costochondritis, esophagitis, systemic vasculitis, sickle cell disease
Coexistence of any disease which limits performance of modified Bruce protocol exercise stress test, e.g., paralysis or amputation of a lower extremity, severe arthritis or lower extremities, severe chronic obstructive pulmonary disease (COPD)

Participation in clinical trials of investigational agents, devices or procedures within thirty days (or scheduled within sixty days of study drug)

Known hypersensitivity to rFGF-2 or related compounds

Any condition which makes the subject unsuitable for participation in this study in the opinion of the investigator, e.g., psychosis, severe mental retardation, inability to communicate with study personnel, drug or alcohol abuse

EXAMPLE 3

"Phase I Clinical Study on Recombinant FGF-2 (SEQ ID NO: 5) Administered to Humans"

Recombinant bFGF-2 of SEQ ID NO: 5 was administered to 52 human patients with severe CAD, who remained symptomatic despite optimal medical management and who refused or were suboptimal candidates for surgical or percutaneous revascularization, in a Phase I open label, single administration, dose escalation, two-site trial. The drug was administered as a single 20 minute infusion divided between two major sources of coronary blood supply (IC), using standard techniques for positioning a catheter into the patient's coronary artery (such as already employed in angioplasty). The doses ($\mu$g/kg) of rFGF-2 administered were 0.33 (n=4), 0.65 (n=4), 2.0 (n=8), 6.0 (n=4), 12.0 (n=4), 24 (n=8), 36 (n=10) and 48 (n=10) of rFGF-2 of SEQ ID NO: 5. Angina frequency and quality of life was assessed by the Seattle Angina Questionnaire (SAQ) at a baseline (before rFGF-2 administration) and at about 60 days after rbFGF-2 administration. Exercise tolerance time (ETT) was assessed by the threadmill test. Rest/exercise nuclear perfusion and gated sestamibi-determined rest ejection fraction (EF), and magnetic resonance imaging (MRI) were assessed at baseline, and at 30 days and 60 days post FGF-2 administration. Other end points that were evaluated included MRI (to objectively measure ejection fraction (EF), normal wall motion (NWM), targeted wall motion (TWM), normal wall thickness (NWT), targeted wall thickness (TWT), ischemic area zone and collateral extent). See Tables 2–4, respectively.

The preliminary safety results indicate that serious events were not dose related. Thus far, of the eight dosage groups, there were three deaths in the lowest dosage groups, i.e., at 0.65 $\mu$g/kg (Day 23), at 2.0 $\mu$g/kg (Day 57) and at 6.0 $\mu$g/kg (Day 63). There were six hospitalizations for acute myocardial infarction (MI) in three patients, i.e., one patient from each of groups 1 (0.33 $\mu$g/kg), 3 (2.0 $\mu$g/kg) and 4 (6.0 $\mu$g/kg). One of the three patients accounted for four of the six hospitalizations for acute MI. There was also one large B cell lymphoma that was diagnosed three weeks after dosing in a patient in group 4. The patient died at two months post dosing. Acute hypotension, seen at higher doses during or just subsequent to infusion, was managed by administration of fluids without need for a vasopressor. The maximum tolerated dose of rFGF-2 (SEQ ID NO: 5) was defined as 36 $\mu$g/kg. Doses of rFGF-2 up to 48$\mu$g/kg IC were managed in patients with aggressive fluid management. However, they were not tolerated due to acute and/or orthostatic hypotension in two out of ten patients. The half-life in humans of the IC infused rFGF-2 was about one hour.

The human patients in this study that were treated with a single IC infusion of rFGF-2 of SEQ ID NO: 5 exhibited a mean increase in ETT of 1.5 to 2 minutes. This is especially significant because an increase in ETT of >30 seconds is considered significant and a benchmark for evaluating alternative therapies, such as angioplasty. The angina frequency and quality of life, as measured by SAQ, showed a significant improvement at 57 days in all five subscales for the 28 patients (n=28) tested. See Tables 2 and 3. In particular, the mean changes in scores for the five criteria evaluated by the SAQ ranged from 13 to 36 with a mean change of 8 or more considered "clinically significant." See Table 2.

Magnetic resonance imaging (MRI) showed objective improvements following administration of a single unit dose of the bFGF-2 of SEQ ID NO: 5, including increased targeted wall motion at 30 and 60 days (p<0.05), and increased targeted wall thickening at 60 days (p<0.01). MRI further showed improved regional wall motion, and increased myocardial perfusion and collateral development in the targeted area for both the lower dose (0.33 $\mu$g/kg and 0.65 $\mu$g/kg) and higher dose (2.0 $\mu$g/kg and 12.0 $\mu$g/kg) groups in an 11 patient test group (n=11).

Abnormal perfusion zone, which was assessed at one of the sites on 28 patients, decreased significantly at 30 and 60 days (p<0.001).

In addition to the above criterion (i.e., ETT SAQ, MRI), a treatment is considered very successful if the angiogenic effects last at least six months. In the present Phase I study, the unexpectedly superior angiogenic effects were observed to last for 57–60 days in all dosage groups. [See Tables 2–4.] Based upon the results already obtained, it is expected that the angiogenic effects would last twelve months or more but at least six months, at which time the procedure could be repeated, if necessary.

EXAMPLE 4

"Proposed Phase II Clinical Study On Recombinant FGF-2 (SEQ ID NO: 5) Administered to Humans to Treat Coronary Artery Disease"

The Phase II clinical trial of rFGF-2 for treating human patients for coronary artery disease is performed as a double blind/placebo controlled study having four arms: placebo, 0.3 $\mu$g/kg, 3 $\mu$g/kg and 30 $\mu$g/kg administered IC.

EXAMPLE 5

"Unit Dose and Pharmaceutical Composition of rFGF-2 for the Phase II Human Clinical Trial"

The rFGF-2 of SEQ ID NO: 5 was formulated as a unit dose and pharmaceutical composition for administration to humans in the Phase II clinical trial referenced herein. The various formulations are described below.

The rFGF-2 Unit Dose was prepared as a liquid in 5 cc type I glass vials with a laminated gray butyl rubber stopper and red flip-off overseal. The rFGF-2 formulation contains 0.3 mg/ml rFGF-2 of SEQ ID NO: 2 in 10 mM sodium citrate, 10 mM monothioglycerol, 0.3 mM disodium dihydrate EDTA (molecular weight 372.2), 135 mM sodium chloride, pH 5.0. Each vial contained 3.7 ml of rFGF-2 drug product solution (1.11 mg rFGF-2 per vial). The resulting unit dose in liquid form is stored at less than −60° C. The above described unit dose is diluted with the "rFGF-2 placebo." Depending on the size of the patient, the contents of several of the vials may be combined to produce a unit dose of 36 $\mu$g/kg for the Phase II study.

The rFGF-2 placebo is supplied as a clear colorless liquid in 5 cc type I glass vials with a laminated gray butyl rubber stopper and red flip-off overseal. The rFGF-2 placebo is indistinguishable in appearance from the drug product and has the following formulation: 10 mM sodium citrate, 10 mM monothioglycerol, 0.3 mM disodium dihydrate EDTA (molecular weight 372.2), 135 mM sodium chloride, pH 5.0. Each vial contains 5.2 ml of rFGF-2 placebo solution. Unlike the unit dose, the rFGF-2 placebo is stored at 2° to 8° C.

The rFGF-2 Pharmaceutical Composition that is infused is prepared by diluting the rFGF-2 unit dose with the rFGF diluent such that the infusion volume is 20 ml for Phase II.

EXAMPLE 6

"Selection Criteria for CAD Patients for the Phase II Human Clinical Trial of IC rFGF-2"

Accordingly, the above described evidence of an unexpectedly superior improvement in quality of life and of increased angiogenic efficacy in humans who were administered a single unit dosage of rFGF-2 in accordance with this invention, supports the patentability of the Applicants' unit dose, pharmaceutical composition and method of using the same.

What is claimed is:

1. A method for treating a human patient for coronary artery disease, comprising administering into one or more coronary vessels in a human patient in need of treatment for coronary artery disease a therapeutically effective amount of a recombinant fibroblast growth factor (FGF) having the sequence set forth in SEQ ID NO:3 or SEQ ID NO:5.

2. The method of claim 1, wherein said therapeutically effective amount administered to said patient is a unit dose of about 0.008 mg to about 6.1 mg of said recombinant FGF.

3. The method of claim 2, wherein said therapeutically effective amount administered to said patient is a unit dose of 0.3 mg to 3.5 mg of said recombinant FGF.

4. The method of claim 1, comprising administering into one or more coronary vessels of said patient about 0.2 μg/kg to about 36 μg/kg of said recombinant FGF.

5. The method of claim 4, comprising administering into one or more coronary vessels of said patient about 0.2 μg/kg to about 2 μg/kg of said recombinant FGF.

6. The method of claim 4, comprising administering into one or more coronary vessels of said patient about 2 μg/kg to about 20 μg/kg of said recombinant FGF.

7. The method of claim 4, comprising administering into one or more coronary vessels of said patient about 20 μg/kg to about 36 g/kg of said recombinant FGF.

* * * * *

UNITED STATES PATENT AND TRADEMARK OFFICE
CERTIFICATE OF CORRECTION

PATENT NO. : 6,451,303 B1
DATED : September 17, 2002
INVENTOR(S) : Whitehouse

It is certified that error appears in the above-identified patent and that said Letters Patent is hereby corrected as shown below:

<u>Title page,</u>
Item [75], Inventors, remove "W. Michael Kavanaugh".

Signed and Sealed this

Twenty-first Day of February, 2006

JON W. DUDAS
*Director of the United States Patent and Trademark Office*